US005665704A

United States Patent [19]

Lowe et al.

[11] Patent Number: 5,665,704

[45] Date of Patent: Sep. 9, 1997

[54] RECEPTOR SPECIFIC ATRIAL NATRIURETIC PEPTIDES

[75] Inventors: David Lowe, Brisbane; Brian C. Cunningham, Piedmont; David Oare, Belmont; Robert S. McDowell, San Francisco; John Burnier, Pacifica, all of Calif.

[73] Assignee: Genentech, Inc., South San Francisco, Calif.

[21] Appl. No.: 451,240

[22] Filed: May 25, 1995

Related U.S. Application Data

[63] Continuation of Ser. No. 362,552, filed as PCT/US94/12591, Nov. 4, 1994, which is a continuation-in-part of Ser. No. 152,994, Nov. 12, 1993.

[51] Int. Cl.$^6$ .......................... C07K 14/58; A61K 38/00

[52] U.S. Cl. .......................... 514/12; 530/324

[58] Field of Search .......................... 530/324; 514/12; 930/50

[56] References Cited

U.S. PATENT DOCUMENTS

| | | | |
|---|---|---|---|
| 4,496,544 | 1/1985 | Needleman | 514/13 |
| 4,609,725 | 9/1986 | Brady et al. | 530/324 |
| 4,673,732 | 6/1987 | Kiso et al. | 530/326 |
| 4,716,147 | 12/1987 | Tjoeng et al. | 514/11 |
| 4,757,048 | 7/1988 | Lewicki et al. | 514/11 |
| 4,764,504 | 8/1988 | Johnson et al. | 514/12 |
| 4,804,650 | 2/1989 | Lewicki et al. | 514/15 |
| 4,816,443 | 3/1989 | Brady et al. | 514/13 |
| 4,861,755 | 8/1989 | Breipohl et al. | 514/11 |
| 4,935,492 | 6/1990 | Lewicki et al. | 530/324 |
| 4,952,561 | 8/1990 | Scolnick et al. | 514/12 |
| 5,017,691 | 5/1991 | Lee et al. | 530/351 |
| 5,057,495 | 10/1991 | Flynn et al. | 514/12 |
| 5,057,603 | 10/1991 | Nutt et al. | 530/324 |
| 5,091,366 | 2/1992 | Nutt et al. | 514/11 |
| 5,095,004 | 3/1992 | Rakhit et al. | 514/12 |
| 5,106,834 | 4/1992 | Bovy et al. | 514/15 |
| 5,159,061 | 10/1992 | Fujino et al. | 530/326 |
| 5,204,328 | 4/1993 | Nutt et al. | 514/13 |
| 5,212,286 | 5/1993 | Lewicki et al. | 530/324 |
| 5,248,764 | 9/1993 | Flanagan et al. | 530/324 |
| 5,418,219 | 5/1995 | Ueda | 514/12 |

FOREIGN PATENT DOCUMENTS

| | | |
|---|---|---|
| 291999 | 11/1988 | European Pat. Off. . |
| 323740 | 7/1989 | European Pat. Off. . |
| 341603 | 11/1989 | European Pat. Off. . |
| 350318 | 1/1990 | European Pat. Off. . |
| 356124 | 2/1990 | European Pat. Off. . |
| 0396474 | 5/1990 | European Pat. Off. . |
| 385476 | 9/1990 | European Pat. Off. . |
| 465097 | 1/1992 | European Pat. Off. . |
| 497368 | 8/1992 | European Pat. Off. . |
| WO85/04870 | 11/1985 | WIPO . |
| WO85/04872 | 11/1985 | WIPO . |
| WO88/03537 | 5/1988 | WIPO . |
| WO88/06596 | 9/1988 | WIPO . |
| WO89/05654 | 6/1989 | WIPO . |
| WO89/10935 | 11/1989 | WIPO . |
| WO90/01940 | 3/1990 | WIPO . |
| WO90/14362 | 11/1990 | WIPO . |
| WO92/06998 | 4/1992 | WIPO . |

OTHER PUBLICATIONS

Rudinger, J. (1976). Peptide Hormones. (ed. J.A. Parsons). University Park Press. Baltimore. pp. 1–7 Jun. 1976.

Bush et al., "Vasorelaxant Potencies and Receptor Binding Affinities of Atrial Natriuretic Hormone (ANH) Analogues" *Fed. Proc.* (Abstract Only) 45:657,2919 (1986).

Cunningham et al., "Production of an Atrial Natriuretic Peptide Variant that is Specific for Type A Receptor" *EMBO Journal* 13(11):2508–2515 (1994).

Dayhoff et al., "A Model of Evolutionary Change in Proteins" *Atlas of Protein Sequence & Structure* 5:89–99 (1972).

Kanagawa et al., "Purification and Complete Amino Acid Sequence of α–Human Atrial Natriuretic Polypeptide (α–hANP)" *Biochem Biophys Res. Comm.* 118(1):131–139 (1984).

Nutt et al., "Chemical Synthesis and Structure–Activity Relations for ANF Analogues" *Endocrinology and Metabolism Clinics of North America* 16(1):19–41 (1987).

Olins et al., "A Linear Analog of Atrial Natriuretic Peptide (ANP) Discriminates Guanylate Cyclase–coupled ANPn Receptors from Non–coupled Receptors" *The Journal of Biological Chemistry* 263(22):10989–10993 (1988).

*Primary Examiner*—Cecilia Tsang
*Assistant Examiner*—Anish Gupta
*Attorney, Agent, or Firm*—Jeffrey S. Kubinec

[57] ABSTRACT

Human receptor selective atrial natriuretic factor variants containing various substitutions, especially G16R, show equal potency and binding affinity for the human A-receptor but have decreased affinity for the human clearance or C-receptor. These ANF variants have natriuretic, diuretic and vasorelaxant activity but have increased metabolic stability, making them suitable for treating congestive heart failure, acute kidney failure and renal hypertension.

14 Claims, 8 Drawing Sheets

RECEPTOR SPECIFIC ATRIAL NATRIURETIC PEPTIDES

This application is a continuation of U.S. Ser. No. 08/362,552 filed Jan. 6, 1995, which is a 35 U.S.C. §371(f) of PCT/US94/12591 filed Nov. 4, 1994, which is a continuation-in-part of U.S. Ser. No. 08/152,994 filed Nov. 12, 1993.

FIELD OF THE INVENTION

The invention relates to synthetic peptides having diuretic, natriuretic, and/or vasodilatory activity in mammals. The peptides of this invention are related to atrial natriuretic peptide. (ANP) but exhibit decreased binding affinity to the natriuretic peptide clearance receptor (NPR-C) and improved stability toward peptidases ("enkephalinase") known to hydrolyze natriuretic peptides.

BACKGROUND OF THE INVENTION

Maintenance of normal extracellular fluid volume depends primarily on the excretion of sodium (natriuresis) and water (diuresis) by the kidneys. These are, in turn, primarily determined by (1) the rate at which plasma is filtered at the glomerulus (glomerular filtration rate, or GFR) and (2) the degree to which sodium is actively reabsorbed along the renal tubule (with water presumably following passively). Sodium reabsorbtion is regulated, in part, by the adrenal steroid hormone aldosterone, in part by blood pressure, hematocrit and plasma viscosity and in part by various atrial natriuretic factors (ANF's) or hormones. (deBold, A. J. et al., *Life Sciences* 28:89–94 [1981]; Garda R., *Experientia* 38:1071–73 [1982]; Currie, M. S. et al. *Science* 221:71–73 [1983]; Flynn T. G. et al., *Biochem. Biophys. Res. Commun.* 117:859–865 [1983]; Currie, M. G. et al., *Science* 223:67–69 [1984]; and Kanagawa, K. et al., *Biochem. Biophys. Res. Commun.* 118:131–139 [1984]).

Atrial natriuretic factors are released as a result of sensors in the atrium responsible for detecting extracellular fluid volume. It is believed that an increase in extracellular fluid volume is detected by these sensors as the atrium stretches to accommodate the increased venous return volume. In response to this stimulus ANF is released into the blood stream where it is transported to the kidney. Binding of ANF to a specific natriuretic peptide receptor (hNPR-A) in the kidney causes inhibition of sodium reabsorbtion along the renal tubule decreasing the reabsorption of water and lowering the extracellular fluid volume.

ANF is also known to be a hypotensive hormone that antagonizes various hypertensive systems including; stimulation of vasoclialation, inhibition of aldosterone secretion from the adrenal gland, renin secretion from the kidney, and the renin-angiotensin II system.

It is known that the serum half-life of ANF's and related peptides (see FIG. 1) that act as hypotensive regulators is relatively short (Crozier, I. G. et al., *The Lancet II* 1242–1245 [1986]) and that these peptides are removed from the blood stream by several mechanisms (FIG. 2). In addition to glomerular filtration two other distinct pathways have been identified which appear to significantly contribute to ANF clearance.

The first of these pathways involves receptor mediated ANF clearance. This pathway is reported to have sufficient capacity to account for about 70–80% of total ANF clearance from the blood stream (Maack, T., et al, *Science* 238:675–678 [1987], EPO Publication No. 233,143). The human natriuretic peptide receptor (hNPR-C) responsible for this clearance is present in many tissues, especially kidney (Luft, F. C. et al., *J. Pharmacol. Exp. Ther.* 236:416–418 [1986]), and promiscuously (Bovy, P. R., *Med. Res. Rev.* 10:1156 [1990]) binds various human natriuretic peptides including hANP, hBNP, and hCNP (FIG. 3). Various synthetic peptides, especially linear peptides (Olins, G. M., et al., *J. Biol. Chem.* 263:10989–10993 [1988]), capable of binding the hNPR-C have been described in the patent literature to enhance the natriuretic, diuretic and vasodilatation activity of endogenous ANF. Therapeutic use of these clearance receptor inhibitors presumably elevates the concentration and thus activity of all hormone peptides cleared by hNPR-C.

A second nonsaturatable clearance pathway also operates to remove serum ANF and is believed to involve the activity of a peptidase, neutral endopeptidase 24.11 (EC 3.4.24.11), also known as "enkephalinase" and referred to herein as NEP (Stevenson, S. L., et al., *Biochem.* 243L183–187 [1987]; Olins, G. M., et al., *Biochim Biophys Acta* 901:97–100 [1987]; Koehn, J. A. et al., *J. Biol. Chem.* 262:11623–11627 [1987]; Yandle, T., et al., *Biochem Biophys Res. Commun.* 146:832–839 [1987]). NEP is present in relatively high amounts in the kidney (Sonnenberg, J. L. et al., *Peptides* 9:173–180 [1988]) and is known to hydrolyze the $Cys^7$-$Phe^8$ amide bond of ANF's (Tamburine, P. P., et al., *Pharm. Exp. Ther.* 251:956–961 [1989]).

It has been observed that inhibitors of NEP, such as thiophan, potentiate the biological responses of administered ANP (Fennell, S. A., et al., *FASEB J* 2:A936 [1988]); Seymour A. A. et al., ibid; Trapani, A. J., et al., ibid; McMartin, C., et al., ibid; Simmerman, M. B. et al. ibid A937). However, administration of nonpeptidyl inhibitors of this pathway, like thiorphan, has the disadvantage that the cerebral NEP or endopeptidase 24.11 ("enkephalinase") will also be inhibited because thiorphan is capable of crossing the blood-brain barrier (Bourgoin, S. et al., *J. Pharm. Exp. Ther.* 238:360–366 (1986). In addition to the use of thiorphan, a variety of other strategies for the inhibition of NEP have been described. These strategies include the use of a metal binding substituent appropriately spaced from the aromatic $Phe^8$ moiety of ANF. Roques., E. P., et al., *Nature* 288:286–288 (1980); see also Gordon, E. M., et al., *Life Sci* 33 (Supplement 1): 113–116 (1983); Mumford, R. M., et al., *Biochem Biophys. Res. Comm.* 109:1303–1309 (1982); Fournie-Zaluski, M. C., et al., *J. Med. Chem.* 26:60–65 (1983); Waksman, G., et al., *Biochem. Biophys. Res. Comm.* 131:262–268 (1985); U.S. Pat. No. 5,248,764. Other strategies also include substitution of unnatural residues for $Phe^8$ such as cyclohexylamine (*Fed. Proc.*, 45:657 [1986]; U.S. Pat. Nos. 5,106,834 and 4,861,755) or N-alkylated amino adds like N-Me-Phe (Nutt et al., EPA 0 465 097). Introduction of D amino adds such as D-Cys or D-Ala has been described (Nutt R. and Veber, D. F. *Endocrin. Metab, Clin. N. Am.*, 16:19–41 [1988]; U.S. Pat. No. 4,816,443) and replacement of amide bonds is described generally by Lewicki et al., U.S. Pat. No. 4,935,492 (see also U.S. Pat. No. 5,095,004).

Because of the obvious therapeutic potential of natriuretic peptides and variants thereof in the treatment of congestive heart failure, hypertension, acute kidney failure etc., numerous synthetic ANF's have been prepared that mimic the biological activity of wild-type ANF but are reported to have improved stability, potency, or duration of action when compared to wild-type ANF. Many of these synthetic ANF's are disclosed in the following U.S. Pat. Nos: 4,496,544; 4,496,544; 4,609,725; 4,673,732; 4,716,147; 4,757,048; 4,764,504; 4,804,650; 4,816,443; 4,861,755; 4,935,492;

4,952,561; 5,057,495; 5,057,603; 5,091,366; 5,095,004; 5,106,834; 5,159,061; 5,204,328; and 5,212,286. In addition, various foriegn documents describing ANF analogs include: WO85/04870; WO85/04872; WO88/03537; WO88/06596; WO89/10935; WO89/05654; WO90/01940; WO90/14362; WO92/06998; EPA 0 323 740; EPA 0 356 124; EPA 0 291 999; EPA 0 350 318; EPA 0 497 368; EPA 0 385 476; and EPA 0 341 603. None of these publications disclose a hANF variant having human receptor specificity (i.e. high affinity for hNPR-A and low affinity for hNPR-C), nor do they disclose the substitutions to hANF(1–28) residues 9, 11, or 16 necessary to achieve this selectivity. Only WO88/03537 discloses a positively charged residue, D-Arg, at position 16 in a truncated form of ANF.

OBJECTS OF THE INVENTION

It is an object of this invention to provide novel compounds having biological activity like hANF(1–28) but with enhanced metabolic stability. It is another object of this invention to provide novel peptides or peptidomimetic compounds having potent vasodilatory, natriuretic, and hypotensive activity. It is a further object to provide novel compounds having enhanced specificity for the hNPR-A in relation to other hNPR's, especially hNPR-B and hNPR-C. These and other objects of the invention will be apparent from the following specification.

SUMMARY OF THE INVENTION

The objectives of this invention have been met by providing novel compounds having potent vasodilatory, natriuretic, and/or hypotensive activity and having enhanced specificity for hNPR-A in relation to other hNPR's, especially hNPR-B and hNPR-C. The compounds of this invention generally have a decreased binding affinity for the human clearance receptor, hNPR-C, compared to the wild-type protein hANF(1–28). These compounds preferably also have an equal or higher affinity for the human A receptor, hNPR-A, compared to the wild-type protein hANF(1–28). These biological characteristics are normally achieved by providing one or more of the following substitutions in wild-type hANF(1–28) or mutants thereof; G9T, G9a, G9R, R11S, R11D, G16R, G16K, G16m and G16Orn. Additionally these compounds have an increased half-life relative to wild-type hANF(1–28) when incubated with neutral endopeptidase 11.24 (NEP). The increased half-life is preferably achieved by; adding the urodilatin amino terminus tetrapeptide sequence, adding a $(Ser)_4$ sequence to the amino terminus, modifying the $Cys^7$-$Phe^8$ amide bond with an amide isostere, N-alkylating $Cys^7$, $Phe^8$, $Ala^{17}$, $Ile^{15}$ or $Phe^{26}$, or inserting a D-amino acid between $Cys^7$ and $Phe^8$. A preferred compound having hNPR-A selectivity is represented by Formula (I)

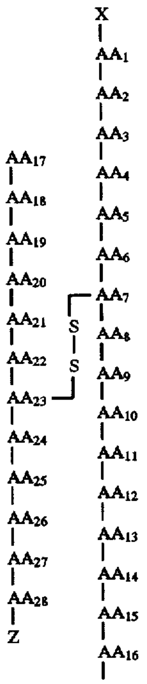

(I)

where

X is selected from

H, $C_1$–$C_6$alkanoyl, Ser-Pro-Lys-, $(Ser)_4$- and Thr-Ala-Pro-Arg-(SEQ ID NO: 1);

$AA_1$ is absent or is selected from

Ser, Met, Gly, Asp, Ala, Tyr and His;

$AA_2$ is absent or is selected from

Leu, Asp, Met, Val, Ser, Ala, Phe, Pro and Lys;

$AA_3$ is absent or is selected from

Cys, Glu, Ser, Gln, His, Gly, Arg and Asp;

$AA_4$ is absent or is selected from

Arg, Gly, Ala, Asp, Met, Leu, Tyr and Pro;

$AA_5$ is absent or is selected from

Ser, Cys and Asp;

$AA_6$ is absent or is selected from

Ser, Gly and Glu;

$AA_7$ is selected from

Cys, N-methyl-Cys, D-Cys and Pen;

$AA_8$ is selected from

Phe, N-methyl-Phe, Trimethylphenyl-Ala, halo(F, Cl, Br and I)phenyl-Ala, Trifluoromethylphenyl-Ala, Tyr, O-methyl-Tyr, Cha, β-napthyl-Ala, α-napthyl-Ala, biphenyl-Ala, diphenyl-Ala, D-Ala, dibenzyl-Ala, florenyl-Ala, adamantyl-Ala, and β-napthyloxy-Ala;

$AA_9$ is selected from

Gly, Arg, Thr, Val, Asp, Ala, D-Ala, Pro and Glu;

$AA_{10}$ is selected from

Gly, Arg, Ser, Ala, His, Pro and Lys;

$AA_{11}$ is selected from

Arg, Lys, N-methyl-Arg, Asp, Ser and Pro;

$AA_{12}$ is selected from

Met, Ile, D-Leu, Nle and Leu;

$AA_{13}$ is selected from

Asp and Glu;

$AA_{14}$ is selected from

Arg, N-methyl-Arg, Pro and Ser;

$AA_{15}$ is selected from

Ile, N-methyl-Ile and Leu;

$AA_{16}$ is selected from

Gly, Tyr, Phe, Ser, Pro and a positively charged amino add residue selected from Orn, Har, Lys, ρ-amidinophenyl-Ala and Arg;

$AA_{17}$ is selected from

Ala, Ser, N-methyl-Ala, and Pro;

$AA_{18}$ is selected from

Gln, Ser and homo-Cys;

$AA_{19}$ is selected from

Ser;

$AA_{20}$ is selected from

Gly and Ala;

$AA_{21}$ is selected from

Leu;

$AA_{22}$ is selected from

Gly and Ala;

$AA_{23}$ is selected from

Cys;

$AA_{24}$ is selected from

Asn;

$AA_{25}$ is selected from

Ser and Val;

$AA_{26}$ is selected from

Phe, D Phe, N-methyl-Phe and Leu;

$AA_{27}$ is selected from

Arg, Orn, Har, Lys, ρ-amidinophenyl-Ala and Arg-Arg;

$AA_{28}$ is selected from

Tyr and homoCys; and

Z is selected from

OH and $NR^1R^2$ where $R^1$ and $R^2$ are independently selected from H, $C_1$–$C_6$alkyl, $C_6$–$C_{12}$aryl and $C_6$–$C_{12}$aryl-$C_1$–$C_6$alkyl;

and where the amide bond (—C(=O)—NH—) bonding residues $AA_7$ and $AA_8$ may optionally be replaced with an amide isostere selected from the group

—$CH_2$—NH—,

—$CH_2$—S—,

—$CH_2$—$S(O)_n$—, where n is 1 or 2,

—$CH_2$—$CH_2$—,

—CH=CH— (E or Z),

—C(=O)—$CH_2$—,

—CH(CN)—NH—,

—C(OH)—$CH_2$—, and

—C—C(=O)—NH— provided that one of $AA_9$, $AA_{11}$, and $AA_{16}$ is selected according to the following scheme $AA_9$ is Arg, Thr or Glu;

$AA_{11}$ is Asp, Ser or Pro; and $AA_{16}$ is a positively charged amino add residue selected from Arg, homoArg (Har), Lys, Orn, and ρ-amidinophenyl-Ala; and pharmaceutically acceptable salts thereof.

Preferably $AA_{16}$ in the compound of Formula I is a positively charged amino acid residue selected from; Orn, Har, Lys, ρ-amidinophenyl-Ala or Arg, and most preferably Arg. Also preferably and independently, $AA_9$ is selected from Arg, Thr, or Glu, and $AA_{11}$ is selected from Asp, Ser, or Pro. Optionally, $AA_3$ is Asp, X is Thr-Ala-Pro-Arg-(SEQ ID NO: 1) and/or the compound may contain a second disulfide (or equivalent) bond.

Optionally, compounds of Formula I may have a D-amino acid residue inserted between $AA_7$ and $AA_8$.

Most preferred hANF variants of this invention include:

hANF(1–28) G9T, R11S, M12I;

hANF(1–28) G9R, R11D, M12I, G16R;

hANF(1–28) G9T, R11S;

hANF(1–28) G9E, G10R, R11P;

hANF(1–28) G10K, R11S;

hANF(1–28) M12I, G16R;

hANF(1–28) G9T, R11S, G16R, Q18P;

hANF(TAPR 1–28) M12I, G16R;

hANF(1–28) M12I, R14S, G16R;

hANF(1–28) G9E, G10R, R11P, M12I, G16R;

hANF(1–28) R3D, G9T, R11S, M12L, R14S, G16R;

hANF(1–28) G9T, R11S, M12I, G16R, inserting D-Ser between residues 7 and 8;

hANF(1–28) G9T, R11S, M12I, G16R, inserting D-Ala between residues 7 and 8;

hANF(TAPR1–28) G13T, R15S, M16I, G20R;

hANF(1–28) F8Cha(1-cyclohexylalanine), G9T, R11S, M12I, G16R;

Mpa(mercaptopropionic acid), F, D-Thr, hANF(10–28), G9T, R11S, M12I, G16R;

Mpa (mercaptopropionic add), F, D-Ala, hANF(10–28), G9T, R11S,

M12I, G16R;

hANF(1–28) C7(N-MeCys), G9T, R11S, M12I, G16R;

hANF(1–28) F8(N-MePhe), G9T, R11S, M12I, G16R;

hANF(1–28) C7F8 replaced by C($\psi CH_2NH$)F*, G9T, R11S, M12I,

G16R;

hANF(1–28) G9(d-Ala), R11D, M12I, G16R;

hANF(1–28) F8Phg(l or d phenyl glycine), G9T, R11S, M12I, G16R; and hANF(1–28) R3D, G9T, R11S, M12L, R14S, G16R, Q18C*, Y28C*.

The invention further comprises a pharmaceutical composition including a pharmaceutically acceptable excipient and any of the compounds described above. This composition is used in a method for inducing naturesis, diuresis, vasodilation or to modulate the renin-angiotensin II and aldosterone systems.

BRIEF DESCRIPTION OF THE FIGURES

In FIG. 4A, "ANP" is Wild-type hANF(1–28) while in FIG. 4B, the "mutant" is hANF(1–28) R3D, G9T, R11S, M12L, R14S, G16R.

| Peptide/ (SEQ ID NO) | Sequence | Half-Life (min.) |
|---|---|---|
| ANF23/(5) | TAPRSLRRSSCFGGRIDRIRAQSGLGCNSFRY | 737 |
| ANF24/(6) | SLRRSSCFGGRIDRIRAQSGLGCNSFRY | 600 |
| ANF40/(7) | SSCvFGGRIDRICFR | 597 |
| ANF50/(8) | SLRRSSCFTGSMDRIGAQSGLGCNSFRY | 93 |
| ANF15 (ratANP)/(9) | SLRRSSCFGGRIDRIGAQSGLGCNSFRY | 165 |
| urodilatin/(2) | TAPRSLRRSSCFGGRMDRIGAQSGLGCNSFRY | 1862 |

Figure 7:
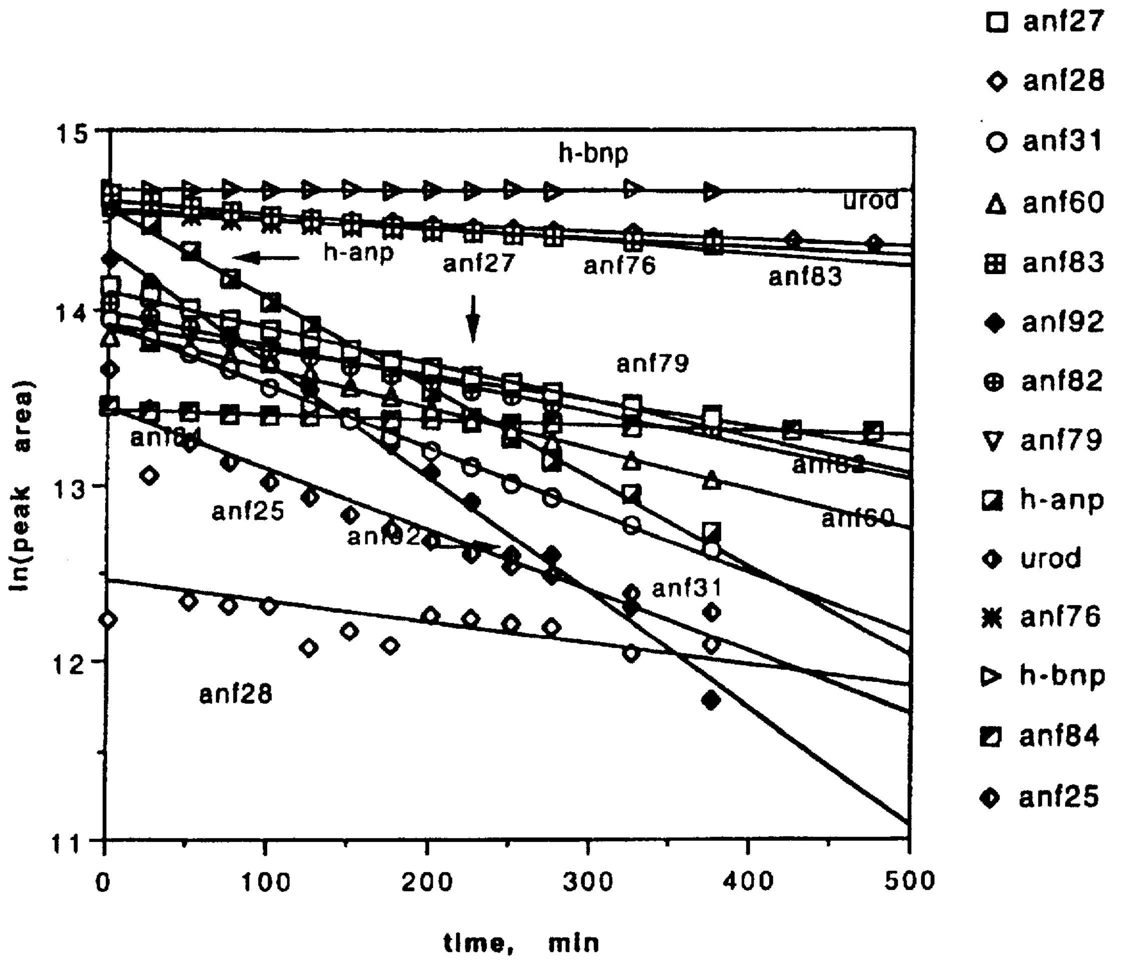

FIG. 7. Degradation of ANF variants (32 nM/ml) by endopeptidase 11.24 (NEP) (0.45 μg/ml). Peptides having the following sequences were assayed as provided in Example 22:

| Peptide/ (SEQ ID NO) | Sequence | Half-Life (min.) |
|---|---|---|
| ANF25/(10) | SLRRSSCFGGRIDSIRAQSGLGCNSFRY | 199 |
| ANF27/(11) | SLRRSSCFTGSIDRIRAQSGLGCNSFRY | 334 |
| ANF28/(12) | SLRRSSCFRGDIDRIRAQSGLGCNSFRY | 571 |
| ANF31/(13) | SLRRSSCFTGSIDRIRAPSGLGCNSFRY | 178 |
| ANF60/(14) | SLRRSSCFGKSMDRIGAQSGLGCNSFRY | 304 |
| ANF76/(15) | TAPRSLRRSSCFTGSIDRIRAQSGLGCNSFRY | 1409 |
| ANF79/(16) | SLRRSSC(Cha)TGSIDRIRAQSGLGCNSFRY | 477 |
| ANF82/(17) | SLRRSS(NMe—C)FTGSIDRIRAQSGLGCNSFRY | 365 |
| ANF83/(17) | SLRRSSC(NMe—F)TGSIDRIRAQSGLGCNSFRY | 932 |
| ANF84/(19) | SLRRSS[CF]*TGSIDRARAQSGLGCNSFRY | 2396 |
| ANF92/(20) | Mpr-FaGDIDRIRAQSGLGCNSFRY | 106 |
| h-ANP/(21) | SLRRSSCFGGRMDRIGAQSGLGCNSFRY | 136 |
| h-BNP/(22) | SPKMVQGSGCFGRKMDRISSSSGLGCKVLRRH | 31726 |
| urodilatin/(2) | TAPRSLRRSSCFGGRMDRIGAQSGLGCNSFRY | 1627 |

*Cys—Phe reduced amide bond

Figure 8:
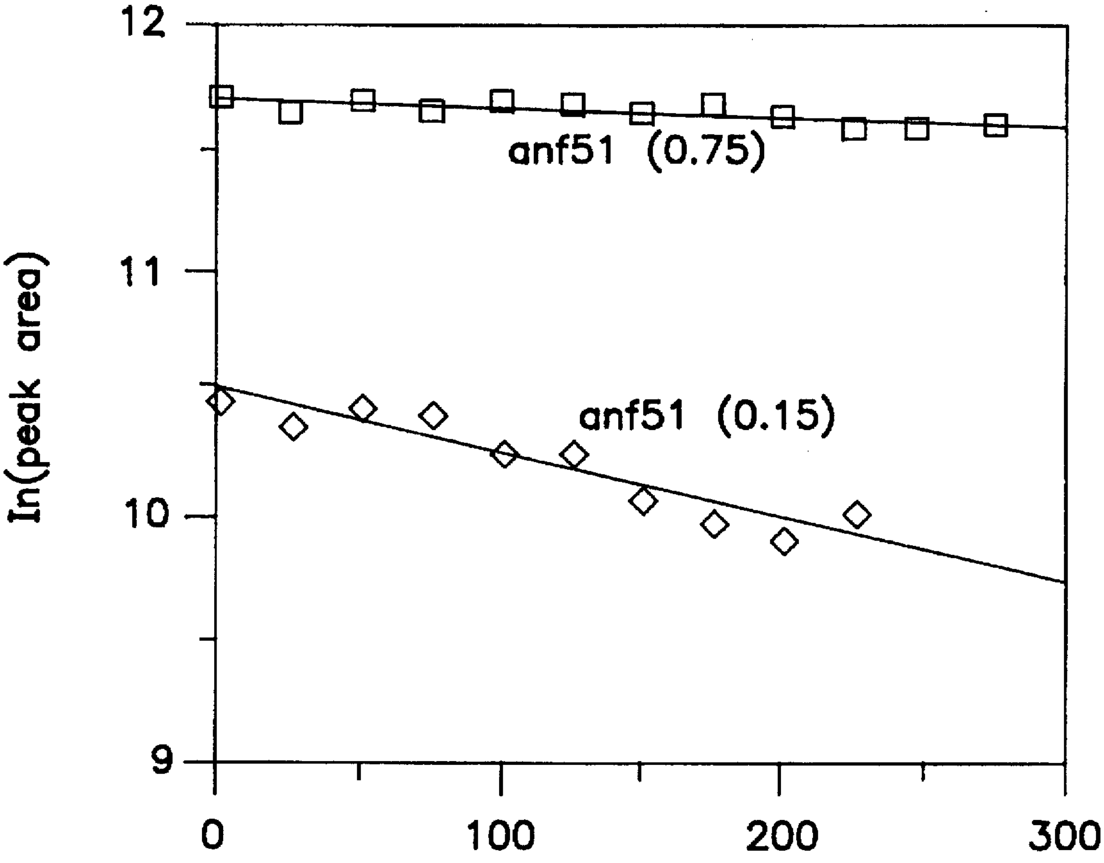

FIG. 8. Degradation of ANF51 (32 nM/ml) by endopeptidase 11.24 (NEP) (0.075 and 0.15 μg/ml). Half-life=1927 min. @0.075 μg/ml NEP and 269 @0.15 μg/ml NEP.

DETAILED DESCRIPTION OF THE INVENTION

A. Definitions

Terms used in the claims and specification are defined as set forth below unless otherwise specified.

The terms "hANF", "hANF(1–28)", α-hANP and "wild-type hANF" are used interchangeably herein and mean the 28 amino acid residue peptide reported by Kangawa et al., *Biochem. Biophys. Res. Comm.* 118(1):131–139 (1984) having the following structure (SEQ D NO: 21)

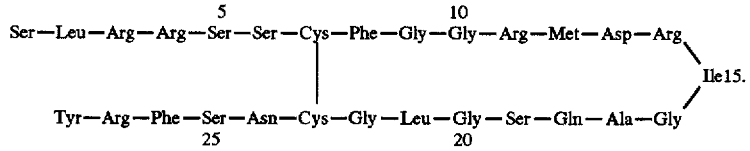

The integers above and below specific residues of this structure define the residue position number. This residue position number is used in conjunction with the one letter amino acid nomenclature, described below, to designate the residue at which a substitution is made in the hANF routants of this invention. Thus for example, when a mutant hANF is synthesized in which arginine (R) replaces glycine (G) at residue position number 16 of wild-type hANF, the nomenclature "hANF G16R" or "hANF(1–28) G16R" is used. Multiple substitutions are designated in the same manner with a comma separating each substitution as exemplified below.

The term "hANF(1–28) G9T, R11S, G16R" designates a triple mutant hANF having that hANF sequence defined above with the substitution of threonine for glycine at residue position 9 (i.e. G9T), the substitution of threonine for glycine at residue position 11 (i.e. R11S), and the substitution of arginine for glycine at position 16 (i.e. G16R). Other mutants are defined in an analogus manner.

The term "hANF(TAPR 1–28) M12I, G16R" designates a double mutant having the tetrapeptide TAPR bonded to the amino group of Ser, residue 1, of hANF.

The term "$C_1$–$C_6$alkyl" means a branched, unbranched or cyclic, saturated aliphatic hydrocarbon radical, having the number of carbon atoms specified. Representative examples of these alkyl radicals include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, cycolhexyl and the like. The terms "lower alkyl" and "$C_1$–$C_6$alkyl" are synonymous and used interchangeably. A preferred "$C_1$–$C_6$alkyl" group is methyl.

The term "$C_1$–$C_6$alkanoyl" encompasses groups such as formyl, acetyl, propionyl, butyryl, isobutyryl, valeryl, isovaleryl, pivaloyl, caproyl, and the like.

The term "$C_6$–$C_{12}$aryl" means a homocyclic hydrocarbon aromatic radical, whether or not fused, having the number of carbon atoms designated. Preferred aryl groups include phenyl, napthyl, biphenyl, phenanthrenyl, naphthacenyl, and the like (see e.g. *Lang's Handbook of Chemistry* (Dean, J. A., ed) 13th ed. Table 7-2 [1985]).

The term "$C_6$–$C_{12}$aryl-$C_1$–$C_6$alkyl" means one, two, or three aryl groups having the number of carbon atoms designated, appended to an alkyl radical having the number of carbon atoms designated including but not limited to; benzyl, napthylmethyl, phenethyl, benzyhydryl diphenylmethyl), florenyl, trityl, and the like. A preferred arylalkyl group is the benzyl group.

Amino acids and amino acid residues described herein may be referred to according to the accepted one or three letter code provided in the table below. Unless otherwise specified these amino acids or residues are of the naturally occurring L stereoisomer form.

| Common Name | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phyenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Norleucine | | Nle |
| Cyclohexylalanine | | Cha |
| Homoarginine | A* | Har |
| Ornithine | | Orn |
| Penicillamine | | Pen |
| Phenyl glycine | | Phg |
| Mercaptopropionic acid | | Mpa |
| D Alanine | a | ala |
| Homocysteine | C* | |

In general, unless otherwise specified, the abbreviations used for the designation of amino acids and the protective groups used therefor are based on recommendations of the IUPAC-IUB Commission of Biochemical Nomenclature (*Biochemistry*, 11:1726–1732 (1972).

The nomenclature used to define compounds of Formula I is that specified by the IUPAC, published in *European Journal of Biochemistry*, 138:9–37 (1984).

"Pharmaceutically acceptable salts" include both add and base addition salts.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, maloneic acid, succinic acid, fumaric acid, tartaric acid, citric acid, benzoic acid, cirmamic acid, mandelic acid, methanesulfonic acid, ethanesulfonic acid, p-toluenesulfonic acid, salicyclic add and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic non-toxic bases are isopropylamine, diethylamine, ethanolamine, trimethamine, dicyclohexylamine, choline, and caffeine.

B. Methods of Making

1. Chemical Synthesis a. General Procedures

One method of producing ANF variants involves chemical synthesis of the polypeptide, followed by treatment under oxidizing conditions appropriate to obtain the native conformation, that is, the correct disulfide bond linkages. This can be accomplished using methodologies well known to those skilled in the art (see Kelley, P. F. & Winkler, M. E. in *Genetic Engineering Principles and Methods*, Setlow, J. K., ed., Plenum Press, N.Y., vol. 12, pp 1–19 [1990]; Stewart, J. M. & Young, J. D. *Solid Phase Peptide Synthesis* Pierce Chemical Co. Rockford, Ill.[1984]; see also U.S. Pat. Nos. 4,105,603; 3,972,859; 3,842,067; and 3,862,925).

Figure 1:
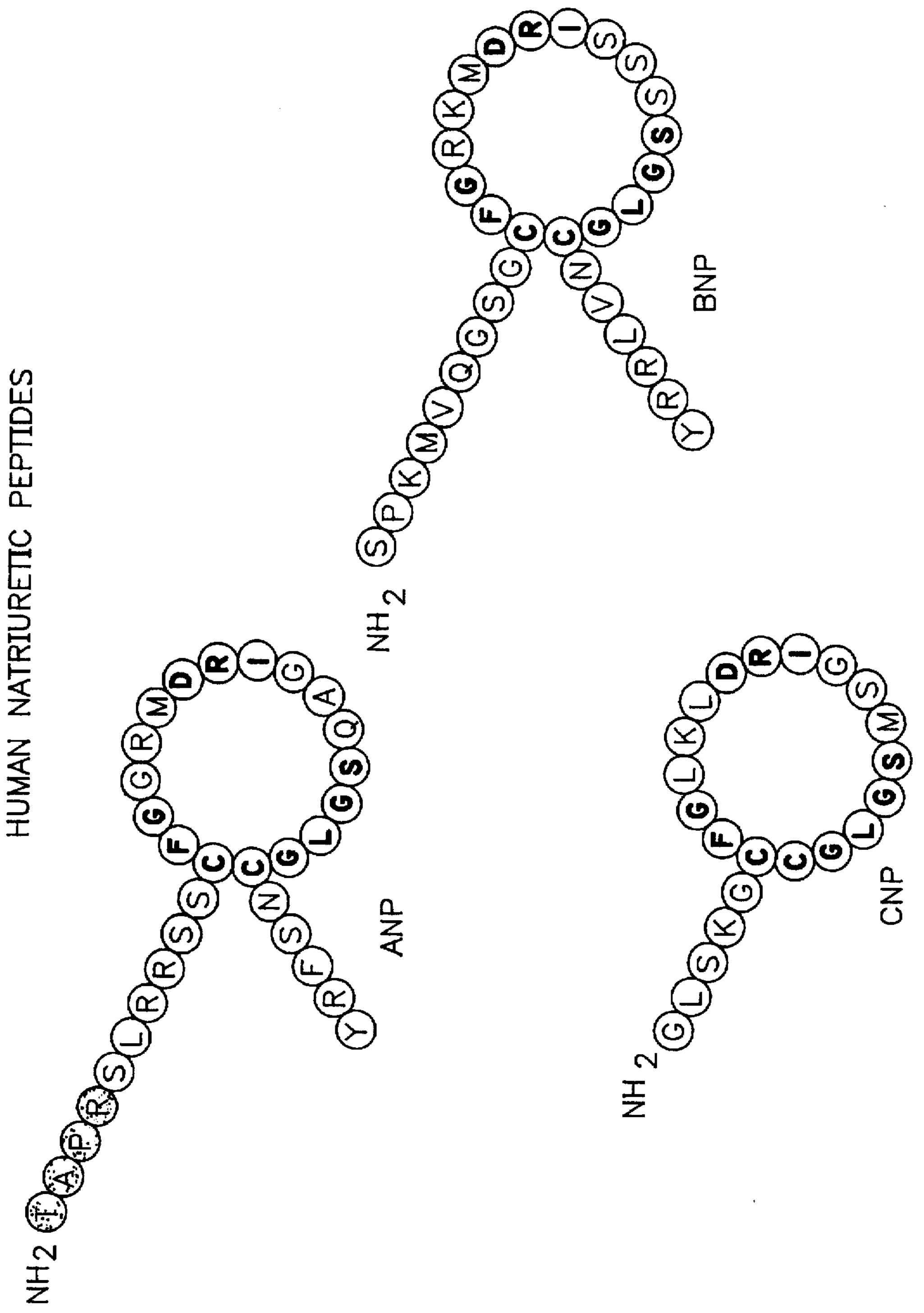
FIG. 1. Sequence of Wild-Type Human Natriuretic Peptides. Dark circles are conserved residues found in all three human hormones (ANP [SEQ ID NO: 2], BNP [SEQ ID NO:3] and CNP [SEQ ID NO: 4]). Shaded circles are additional amino-terminus residues found in a kidney-specific human ANF variant named "Urodilatin". Unshaded circles are residues not conserved among the human natriuretic hormones.
Figure 2:
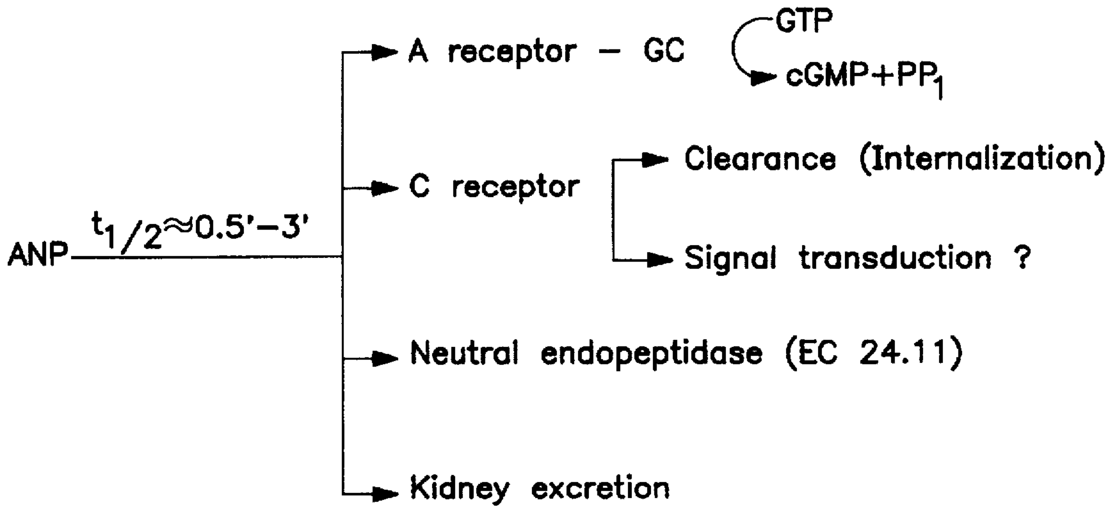
FIG. 2. The four fates of ANF (or ANP) primarily responsible for its short serum half-life ($t_{1/2}$).
Figure 3:
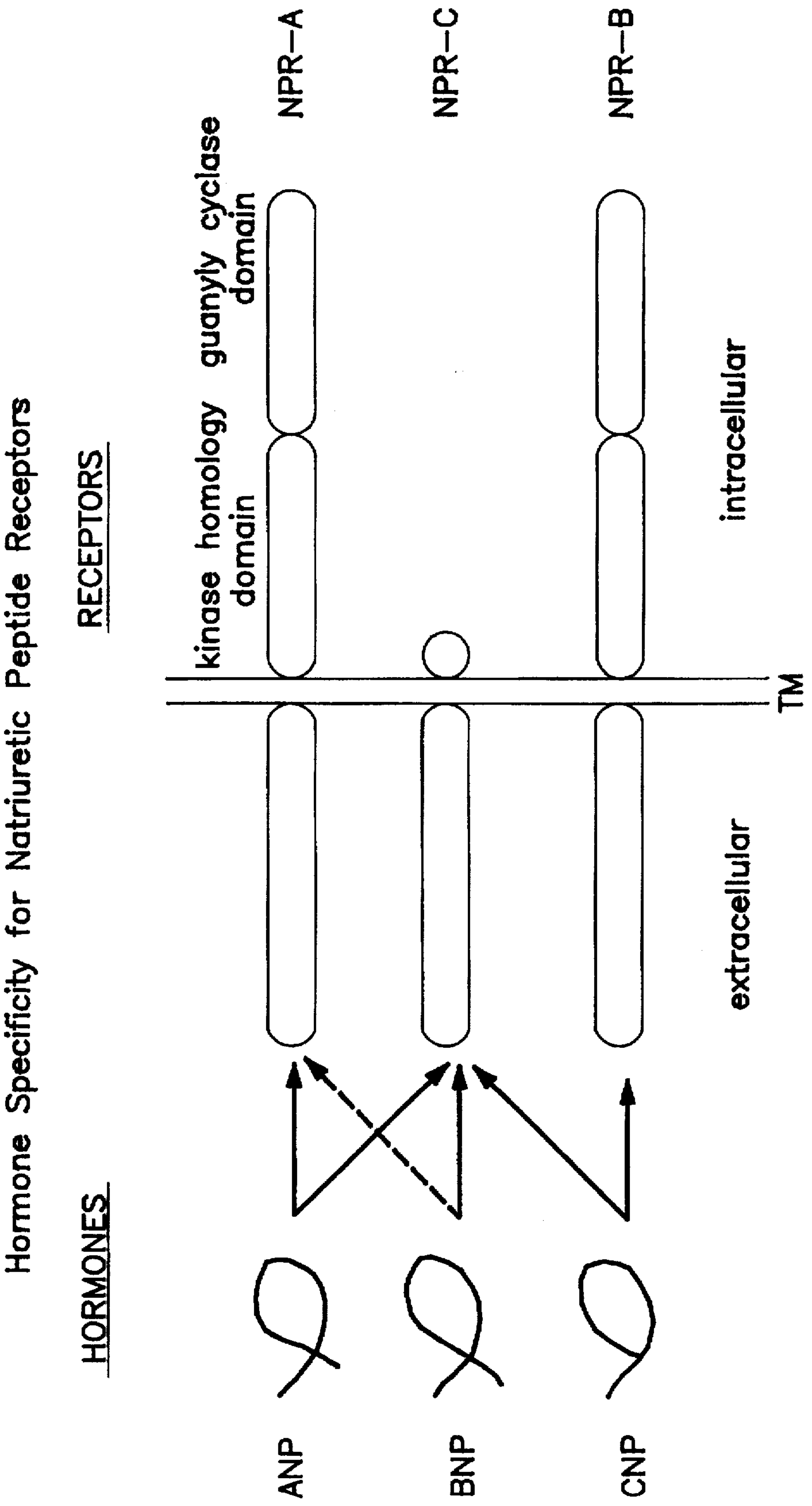
FIG. 3. Hormone Specificity for Known Natriuretic Peptide Receptors. Solid arrow indicates a strong binding affinity. Dashed arrow indicates a weak binding affinity. The A-receptor (NPR-A) is found predominantly in the adrenal cortex and kidney, the B-receptor (NPR-B) is found predominantly in the atrium of the heart and the central nervous system, while the C-receptor is found primarily in endothelial tissue of the kidney. All three receptors have homologous extracellular domains containing about 440 residues. The C-receptor contains only a small vestigal 37 amino acid intracellular domain of unknown function, while the A- and B-receptors both have guanyl cyclase and tyrosine kinase domains. It is believed the A-receptor is responsible for most of the hormone's hypotensive effects and the C-receptor mediates its rapid clearence.

Polypeptides of the invention may be conveniently prepared using solid phase peptide synthesis (Merrifield, *J. Am. Chem. Soc.*, 85:2149 [1964]; Houghten, *Proc. Natl. Acal. Sci. U.S.A.* 82:5132 [1985]). Solid phase synthesis begins at the carboxy-terminus of the putative peptide by coupling a protected amino acid to a suitable resin (e.g. chloromethylated polystyrene resin) as shown in FIGS. 1-1 and 1-2, on pages 2 and 4 of Stewart and Young supra. After removal of the α-amino protecting group with, for example, trifluoroacetic acid (TFA) in methylene chloride and neutralizing in, for example TEA, the next α-amino- and side-chain protected amino acid in the synthesis is added. The remaining α-amino- and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as the azide method, mixed acid anhydride method, DCC (N,N'-dicyclohexylcarbodiimide) or DIC (N,N'-diisopropylcarbbodiimide)methods, active ester method (p-nitrophenyl ester method, BOP [benzotriazole-1-yl-oxy-tris (dimethylamino) phosphonium hexafluorophosphate] method, N-hydroxysuccinic acid imido ester method, etc, and Woodward reagent K method.

Common to chemical syntheses of peptides is the protection of any reactive side-chain groups of the amino acids with suitable protecting groups. Ultimately these protecting groups are removed after the desired polypeptide chain has bean sequentially assembled. Also common is the protection of the α-amino group on an amino acid or a fragment while that entity reacts at the carboxyl group followed by the selective removal of the α-amino-protecting group to allow subsequent reaction to take place at that location. Accordingly, it is common in polypeptide synthesis that an intermediate compound is produced which contains each of the amino acid residues located in the desired sequence in the peptide chain with various of these residues having side-chain protecting groups attached. These protecting groups are then commonly removed substantially at the same time so as to produce the desired resultant product following removal from the resin.

Suitable protective groups for protecting the α- and ε-amino side chain groups are exemplified by benzyloxycarbonyl (abbreviated Z), isonicotinyloxycarbonyl (iNOC), O-chlorobenzyloxycarbonyl [Z(2Cl)], p-nitrobenzyloxycarbonyl [$Z(NO_2)$], p-methoxybenzyloxycarbonyl [Z(OMe)], t-butoxycarbonyl, (Boc), t-amyloxycarbonyl (Aoc), isoborrnyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

Protective groups for the carboxy functional group are exemplified by; benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group of cysteine may be protected with p-methoxybenzyl, triphenylmethyl, acetylaminomethyl ethylcarbamoyle, 4-methylbenzyl, 2, 4, 6-trimethy-benzyl (Tmb) etc, and the hydroxyl group of serine can be protected with benzyl, t-butyl, acetyl, tetrahydropyranyl and the like.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino add sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic add, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 μM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

b. Non-peptide (anide isostere) Linkages

In one embodiment of the invention, the amide linkages (—C(=O)—NH—) are replaced with amide isostere linkages such as; $-CH_2-NH-$, $-CH_2-S-$, $-CH_2-O-$, $-CH_2-CH_2-$, $-CH=CH-$ (cis and trans), $-C(=O)-CH_2-$, $-CH(OH)-CH_2-$, $-CH(CN)-NH-$, $-O-C(=O)-NH-$ and $-CH_2-SO-$, by methods known in the art. The following references describe preparation of peptide analogs which include these alternative-linking moieties: Spatola, A. F., Vega Data 1(3): "Peptide Backbone Modifications" (General Review) (March 1983), Spatola, A. F., in "Chemistry and biochemistry of Amino Acids Peptides and Proteins", B. Weinstein, ed., Marcel Dekker, New York, P. 267 (1983); Morley, J. S., *Trends Pharm. Sci.* pp. 463–468; Hudson, D. et al. *Int. J. Pept. Prot. Res.* 14:177–185 (1979) ($-CH_2NH-$, $-CH_2CH_2-$); Tourwe, D., et al., *Structural Biology* 331–333 (1989) (E, $-CH=CH-$); Spatola, A. F., et al., *Life Sci.* 38:1243–1249 (1986) ($-CH_2-S-$); Hann, M. M., *J. Chem. Soc. Perkin. Trans.* 1307–314 (1982) ($-CH=CH-$, cis and trans); Almquist, R. G., et al., *J. Med. Chem.* 23:1392–1398 (1980) ($-C(=O)-CH_2-$); Jennings-White C., et al., *Tetrahedron Lett* 23:(1982) ($-C(=O)-CH_2-$); Szelke, M., et al., EP Application No. 45665 (1982) *Chem Abs*:9739405 (1982) ($-CH(OH)-CH_2$); Holladay, M. W., et al., *Tetrahedron Lett* 24:4401–4404 (1983) ($-C(OH)-CH_2-$); Hruby, V. J. *Life Sci* 31:189–199 (1982) ($-CH_2S-$); and Cho, C. Y. et al, *Science* 261:1303–1305 (1993) ($-O-C(=O)-NH-$).

2. Recombinant Synthesis

In a further embodiment, the present invention encompasses a composition of matter comprising isolated nucleic acid, preferably DNA, encoding the protein component of a composition of matter comprising a polypeptide selected from ANF variants that contain the amino acid substitutions described in Table I. The invention further comprises an expression control sequence operably linked to the DNA molecule, an expression vector, preferably a plasmid, comprising the DNA molecule, where the control sequence is recognized by a host cell transformed with the vector.

Preferred expression vectors of the present invention may be selected from; pBR322, phGH1, pBO475, pB1537, pRIT5, pRIT2T, pKK233-2, pDR540, pPL-lambda and pB1537, with the most preferred vector being pB1537.

Preferred host cells containing the expression vector of the present invention may be selected from *E. coli* K12 strain 294 (ATCC No. 31446), *E. coli* strain JM101, *E. coli* B, *E. coli* X1776 (ATCC No. 31537), *E. coli* c600, *E. coli* W3110 (F-, gamma-, prototrophic, ATCC No. 27325), *Bacillus subtilis, Salmonella typhimurium, Serratia marcesans,* and Pseudomonas species, with the most preferred host cell being *E. coli* W3110 (ATCC No. 27325), or a derivative thereof such as the protease deficient strain 34B8.

The composition of the present invention may be made by a process which includes the steps of isolating or synthesizing (by art standard techniques) nucleic add sequences encoding any of the amino acid sequences described herein, ligating the nucleic acid sequence into a suitable expression vector capable of expressing the nudeic acid sequence in a suitable host, transforming the host with the expression vector into which the nucleic acid sequence has been ligated, culturing the host under conditions suitable for expression of the nudeic acid sequence, whereby the protein encoded by the selected nucleic acid sequence is expressed by the host. In this process, the ligating step may further contemplate ligating the nucleic acid into a suitable expression vector such that the nudeic acid is operably linked to a suitable secretory signal, whereby the amino acid sequence is secreted by the host. The secretory signal may be selected from the group consisting of the leader sequence of stII, ecotin, lamB, herpes gD, lpp, alkaline phosphatase, invertase, and alpha factor and is preferably stII.

a. Gene Synthesis, Cloning, and Expression

1. General Procedures

From the purified protein and its amino acid sequence, ANF or ANF variants may be produced using recombinant DNA techniques. These techniques contemplate, in simplified form, taking a gene encoding either ANF or ANF variants; inserting it into an appropriate vector; inserting the vector into an appropriate host cell; culturing the host cell to cause expression of the ANF or ANF variants gene; and purifying the protein produced thereby.

Somewhat more particularly, the DNA sequence encoding either ANF or ANF variants is cloned and manipulated so that it may be expressed in a convenient host. DNA encoding parent polypeptides can be obtained from a genomic library, from cDNA derived from mRNA from cells expressing ANP or ANP homologs, or by synthetically constructing the DNA sequence (Sambrook, J. et al., *Molecular Cloning* (2nd ed.), Cold Spring Harbor Laboratory, N.Y. [1989]).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which en&ode proteins that are capable of providing phenotypic selection in transformed cells.

For example, *E. coli* may be transformed using pBR322, a plasmid derived from an *E. coli* species (Mandel, M. et al, *J. Mol. Biol* 53:154 [1970]). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

2. Direct Expression of ANF or ANF Variants

A preferred vector for direct expression is pB1537. This vector was created as described in Example 23–25 and contains origins of replication for *E. coli*, the alkaline phosphatase promoter, the stII signal sequence, the ANP gene, and the ampicillin resistance gene. Other preferred vectors are pR1T5 and pR1T2T (Pharmacia Biotechnology). These vectors contain appropriate promoters followed by the Z domain of protein A, allowing genes inserted into the vectors to be expressed as fusion proteins. Further discussion of these vectors may be found below.

Other preferred vectors can be constructed using standard techniques by combining the relevant traits of the vectors described herein as illustrated in Example 23–25. In this instance a vector containing the origins of replication for phage and *E. coli*, which allow it to be shuttled between such hosts, was used thereby facilitating both mutagenesis and expression (Cunningham, B., et al., *Science* 243:1330–1336 [1989]; Wells, J. & Cunningham, B., WO 90/04788 published 3 May 1990). Relevant traits of the vector include the promoter, the ribosome binding site, the ANF or ANF variant gene or gene fusion (the Z domain of protein A and ANF or ANF variant and its linker), the signal sequence, the antibiotic resistance markers, the copy number, and the appropriate origins of replication.

ANF or ANF variants have been expressed in *E coli* strain 34B8 using a plasmid with the alkaline phosphatase promoter and the stII signal sequence. This resulted in an expression system in which about 12 mg/L of an ANP variant containing the mutations R3D/G9T/R11S/M12L/R14S/G16R and about 3 mg/L of an ANF variant containing just the R3D mutation were secreted into the broth of 10 liter fermentions. Shake flask experiments showed these mutants expressed dramatically higher than wild-type ANF (about 3200 and 800 times greater, respectively). However, by expressing wild-type ANF in a different strain, *E coli* 23G3, its expression could be increased about 15 fold.

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtills,* and other enterobacteriaceae such as *Salmonella typhimurium* or *Serratia marcesans,* and various pseudomonas species. The preferred prokaryote is *E. coli* W3110 (ATCC 27325). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture,* Academic Press, Kruse and Patterson, editors (1973)). Examples of such useful host cell lines are VERO and HeLa cells, Chinese Hamster Ovary (CHO) cell lines, W138, 293, BHK, COS-7 and MDCK cell lines.

Specifically, in the instant case, the ANF gene was assembled from synthetic oligonucleotides and inserted into a convenient expression vector. The resulting plasmid, pB1537, places the transcription of the ANF gene under the control of the alkaline phosphatase promoter (AP) and translation under control of the tryptophan Shine-Dalgamo sequence. The stII signal sequence was used to secrete ANF into the *E. coli* periplasm.

3. Gene Fusions

A variation on the above procedures contemplates the use of gene fusions, wherein the gene encoding ANF or ANF variant is associated, in the vector, with a gene encoding another protein or a fragment of another protein. This results in ANF or ANF variants being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering,* Williamson, R., Ed., Academic, London, Vol. 4, p. 127[1983]; Uhlen, M. & Moks, T., *Methods Enzymol.* 185:129–143 [1990]). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144–161 [1990]). It has also been shown that many heterologous proteins are degraded when expressed directly in *E. coli,* but are stable when expressed as fusion proteins (Marston, F. A. O., *Biochem J.* 240:1 [1986]).

ANF or ANF variants expressed as fusion proteins may be properly folded or may require folding to obtain the native structure. The properly folded fusion protein may be active and useful as pharmaceutical drug. More preferred would be the correctly folded native protein that is obtained from the fusion protein by methods known in the art. Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino adds may be inserted just prior to the 5' end of the ANF or ANF variant gene.

Alternatively, one can employ proteolytic cleavage of fusion proteins, which has been recently reviewed (Carter, P. (1990) in *Protein Purification: From Molecular Mechanisms to Large-Scale Processes,* Ladisch, M. R., Willson, R. C., Paton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g. the Z domain of protein A) and the protein of interest, such as ANF or an ANF variant. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The protein may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the protein is treated with a chaotrope, such a guanidine HCl, and is then treated with a redox buffer, containing, for example, reduced and oxidized dithiothreitol or glutathione at the appropriate ratios, pH, and temperature, such that the protein of interest is refolded to its native structure.

4. Mutant DNA Production

As previously discussed, various techniques are also available which may now be employed to produce mutant ANF or an ANF variant DNA, which encodes for additions, deletions, or changes in amino acid sequence of the resultant protein relative to the parent ANF molecule.

By way of illustration, with expression vectors encoding ANF in hand, site specific mutagenesis (Kunkel et al.,

*Methods Enzymol* 204:125–139 [1991]; Carter, P., et al., *Nucl Acids Res.* 13:4331 [1986]; Zoller, M. J. et al., *Nucl. Acids Res.* 10:6487 [1982]), cassette mutagenesis (Wells, J. A., et al., *Gene* 34:315 [1985]), restriction selection mutagenesis (Wells, J. A., et al., *Philos. Trans, R. Soc. London SerA* 317, 415 [1986]) or other known techniques may be performed on the ANF DNA. The mutant DNA can then be used in place of the parent DNA by insertion into the aforementioned expression vectors. Growth of host bacteria containing the expression vectors with the mutant DNA allows the production of mutant ANF, which can be isolated as described herein.

Specifically, in the present case, 2 routants of ANF that substituted aspartic acid at position 3 of ANF for arginine were expressed at dramatically higher levels in *E coli* than wild-type ANF. Additionally, one of these variants that further reduced the basicity of ANF with the mutations R11S and R14S showed the highest level of expression.

b. Purification and Characterization

Purification and characterization of ANF or ANF variants may be carried out by any art standard technique. In the instant case, recombinant mutant ANF (containing the mutations R3D/G9T/R11S/M12L/R14S/G16R) was purified from the broths of *E. coli* cultures grown in 10 liter fermentors by batch reverse phase chromatography, cation exchange chromatography and C18 reverse phase HPLC. Approximately 6 mg of purified ANP mutant per liter of fermentation broth was isolated using this method. The identity of the purified recombinant ANF was verified by mass spectral analysis (3026+/−0.4 amu, obs.; 3026 amu, calcd.) and amino acid analysis. The purified ANT appeared to be >95% homogeneous based on reverse phase HPLC. Amino acid analysis of the variants was within experimental error of that calculated from the sequence.

C. Discovery and Preferred Embodiments

In the course of screening ANF variants in a competition screen for human ANF receptors (hNPR-A vs hNrPR-C) a number of unique amino acid substitutions were identified that conferred hNPR-A specificity. Somewhat surprisingly, variants identified in this way, enriched for human NPR-A binding, did not bind rat NPR-A. This species specificity for the variants is consistent with the known sequence difference between rat and human "A" receptors and points out the danger of using receptors other than those of the host in screening for variant ANF's having improved pharmacological properties.

Preferred compounds of this invention are synthetic hormone agonists of the human natriuretic peptide receptor-A (hNPR-A). This receptor is found in kidney, smooth muscle, adrenal and other tissues (Napier M. A. et al, *Proc. Nat. Acad. Sci. U.S.A.*, 81:5946–5950 (1984), and contains an intracellular guanyl cyclase domain. The action of hNPR-A is mediated by hydrolysis of GTP to produce the second messenger cGMP. Accordingly, preferred compounds of this invention stimulate hNPR-A to produce cGMP to at least the same extent as wild-type ANF.

The preferred compounds of this invention do not however bind to the human natriuretic peptide clearance receptor-C (hNPR-C) to the same extent as wild-type ANF. Rather they bind to the hNPR-C with less than 50% and more preferably less than 10% of the affinity of wild-type ANF. This is preferably achieved by substituting residues: T, R and E at position residue 9; S, D and P at position residue 11; and/or R (or another positively charged residue) and sometimes Y at residue position 16 in hANF(1-28).

For assay systems to measure binding of hANF and the compounds of this invention to hNPR-C see: Schank, D. B., et al., *Biochem. Biophys. Res. Comm.* 127:433–442 (1985); Scarborough, R. M., *J. Biol. Chem.* 261:12960–12964 and WO 90/01940.

The preferred compounds of this invention are also resistant to hydrolysis by NEP or neutral endopeptidase 24.11 CEC3.4.24.11). This is preferably achieved through stabilizing the $Cys^7$-$Phe^8$ amide bond by replacing it with an amide isostere. Alternatively or additionally, endopeptidase resistance can be improved by adding additional residues to the amino terminus, such as the "urodilatin" TAPR sequence, or by introducing a second crosslinking site into hANF(1-28) or variants thereof. An example of the latter, namely adding a second crosslinking site may be achieved by substituting homoCys into positions 18 and 28 and oxidizing them to form a second disulfide.

In view of the foregoing, most preferred hANF variants include:

hANF(TAPR 1-28) M121, G16R (SEQ ID NO: 5)

T—A—P—R—S—L—R—R—S—S—C—F—G—G—R—I—D—R—I—R—A—Q—S—G—L—G—C—N—S—F—R—Y,

S—S hANF(1-28) M121, G16R (SEQ ID NO: 6)

S—L—R—R—S—S—C—F—G—G—R—I—D—R—I—R—A—Q—S—G—L—G—C—N—S—F—R—Y,

S—S hANF(1-28) G9T, R11S, M12I (SEQ ID NO: 23)

S—L—R—R—S—S—C—F—T—G—S—I—D—R—I—R—A—Q—S—G—L—G—C—N—S—F—R—Y,

S—S hANF(1-28) G9R, R11D, M12I, G16R (SEQ ID NO: 12)

S—L—R—R—S—S—C—F—R—G—D—I—D—R—I—R—A—Q—S—G—L—G—C—N—S—F—R—Y,

S — S hANF(1-28) G9T, R11S, G16R, Q18P (SEQ ID NO: 24)

-continued

S—L—R—R—S—S—C—F—T—G—S—M—D—R—I—R—A—P—S—G—L—G—C—N—S—F—R—Y,
(S—S bridge between C and C)

hANF(1–28) G9T, R11S (SEQ ID NO: 8)

S—L—R—R—S—S—C—F—T—G—S—M—D—R—I—G—A—Q—S—G—L—G—C—N—S—F—R—Y,
(S—S bridge between C and C)

hANF(1–28) G9E, G10R, R11P (SEQ ID NO: 25)

S—L—R—R—S—S—C—F—E—R—P—M—D—R—I—G—A—Q—S—G—L—G—C—N—S—F—R—Y,
(S—S bridge between C and C)

hANF(1–28) G10K, R11S (SEQ ID NO: 14)

S—L—R—R—S—S—C—F—G—K—S—M—D—R—I—G—A—Q—S—G—L—G—C—N—S—F—R—Y,
(S—S bridge between C and C)

hANF(1–28) R3D, G9T, R11S, M12L, R14S, G16R (SEQ ID NO: 26)

S—L—D—R—S—S—C—F—T—G—S—L—D—S—I—R—A—Q—S—G—L—G—C—N—S—F—R—Y,
(S—S bridge between C and C)

hANF(1–28) G9T, R11S, M12I, G16R, inserting D—Ser between residues 7 and 8 (SEQ ID NO: 27)

S—L—R—R—S—S—C—(D—Ser)—F—T—G—S—I—D—R—I—R—A—Q—S—G—L—G—C—N—S—F—R—Y,
(S—S bridge between C and C)

hANF(1–28) G9T, R11S, M12I, G16R, inserting D—Ala between residues 7 and 8 (SEQ ID NO: 28)

S—L—R—R—S—S—C—(D—Ala)—F—T—G—S—I—D—R—I—R—A—Q—S—G—L—G—C—N—S—F—R—Y,
(S—S bridge between C and C)

urodilatin (1–32) G13T, R15S, M16I, G20R (SEQ ID NO: 15)

T—A—P—R—S—L—R—R—S—S—C—F—T—G—S—I—D—R—I—R—A—Q—S—G—L—G—C—N—S—F—R—Y,
(S—S bridge between C and C)

hANF(1–28) F8Cha (1-cyclohexylalanine), G9T, R11S, M12I, G16R (SEQ ID NO: 16)

S—L—R—R—S—S—C—(1—Cha)—T—G—S—I—D—R—I—R—A—Q—S—G—L—G—C—N—S—F—R—Y,
(S—S bridge between C and C)

Mpa (mercaptopropionic acid), hANF(8–28) G9(D—Thr), R11S, M12I, G16R (SEQ ID NO: 29)

Mpa—F—(D—Thr)—G—S—I—D—R—I—R—A—Q—S—G—L—G—C—N—S—F—R—Y,
(S—S bridge between Mpa and C)

Mpa (mercaptopropionic acid), hANF(8–28) G9(D—Ala), R11S, M12I, G16R (SEQ ID NO: 30)

Mpa—F—(D—Ala)—G—S—I—D—R—I—R—A—Q—S—G—L—G—C—N—S—F—R—Y,
(S—S bridge between Mpa and C)

hANF(1–28) C7(N—MeCys), G9T, R11S, M12I, G16R (SEQ ID NO: 31)

S—L—R—R—S—S—(N—MeCys)—F—T—G—S—I—D—R—I—R—A—Q—S—G—L—G—C—N—S—F—R—Y,
(S—S bridge between N—MeCys and C)

hANF(1–28) F8(N—MePhe), G9T, R11S, M12I, G16R (SEQ ID NO: 32)

S—L—R—R—S—S—C—(N—MePhe)—T—G—S—I—D—R—I—R—A—Q—S—G—L—G—C—N—S—F—R—Y,
(S—S bridge between C and C)

hANF(1–28) C7F8 replaced by C(ψ$CH_2$NH)F*, G9T, R11S, M12I, G16R (SEQ ID NO: 33)

S—L—R—R—S—S—C(ψ$CH_2$NH)F—T—G—S—I—D—R—I—R—A—Q—S—G—L—G—C—N—S—F—R—Y,
(S—S bridge between C and C)

*C(ψ$CH_2$NH)F represents the peptide segment derived from the amino acid below:

-continued

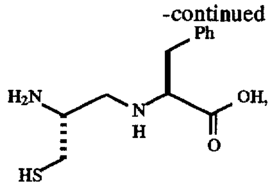

hANF(1-28) G9(D-Ala), R11D, M12I, G16R (SEQ ID NO: 34)

S—L—R—R—S—S—C—F—(D—Ala)—G—D—I—D—R—I—R—A—Q—S—G—L—G—C—N—S—F—R—Y,
S—S hANF(1-28) F8Phg(D or L phenylglycine), G9T, R11S, M12I, G16R (SEQ ID NO: 35)

S—L—R—R—S—S—C—Phg—T—G—S—I—D—R—I—R—A—Q—S—G—L—G—C—N—S—F—R—Y,
S—S and hANF(1-28) R3D, G9T, R11S, M12L, R14S, G16R, Q18C*, Y28C* (SEQ ID NO: 36)

S—L—D—R—S—S—C—F—T—G—S—L—D—S—I—R—A—C*—S—G—L—G—C—N—S—F—R—C*.
S—S
S—S

D. Biological Activity

Figure 4A:
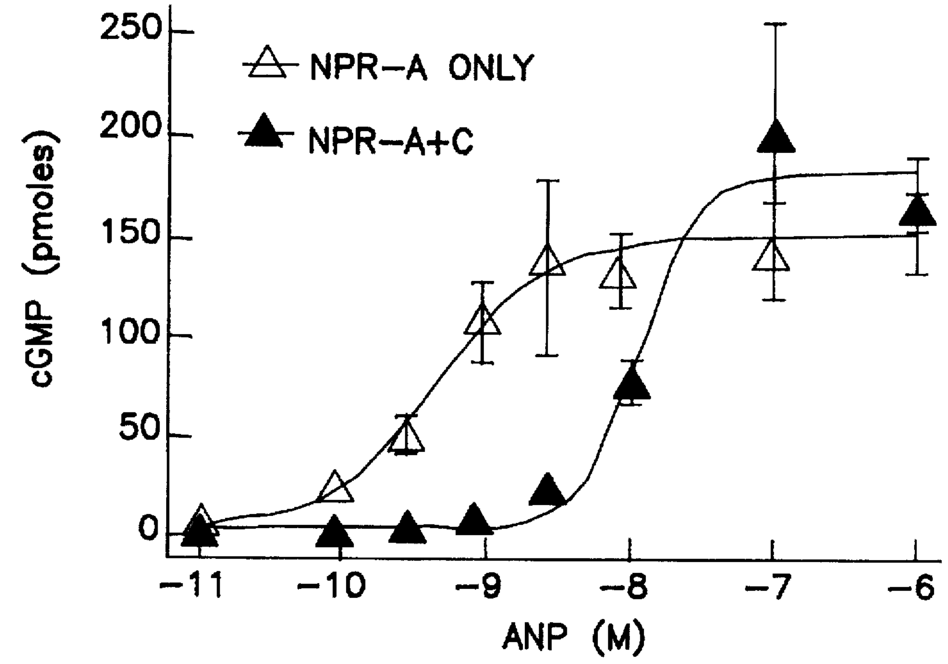
FIGS. 4A and 4B. Resistance to inactivation of ANF variants by cells expressing hNPR-C.
Figure 4B:
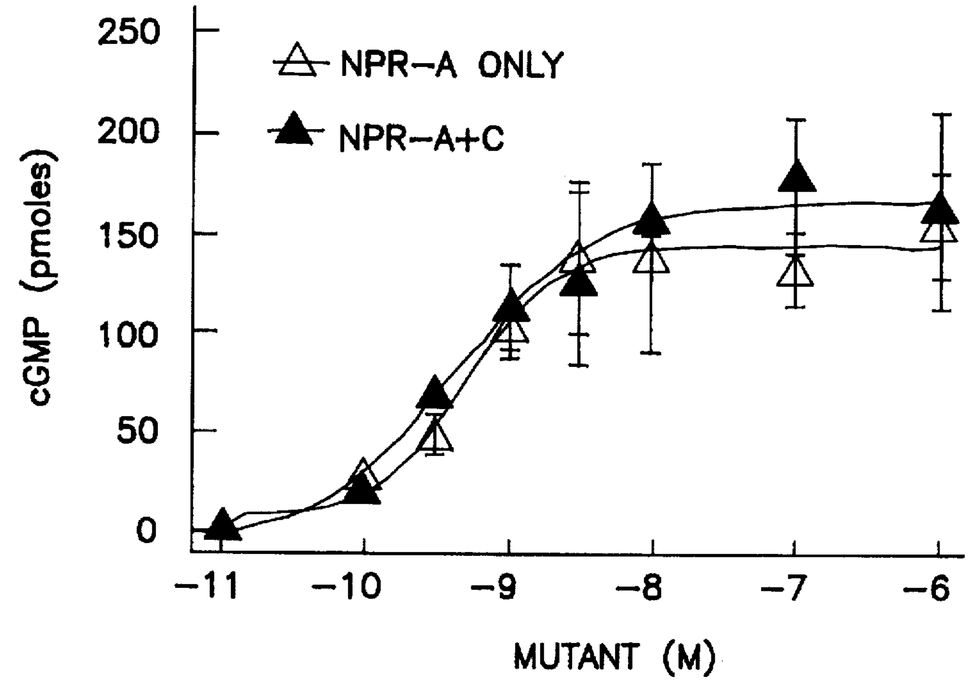

Receptor specific variants of the vasoactive hormone hANF(1-28) have been isolated that stimulate cellular hNPR-A guanyl cyclase activity and block hormone clearance mediated by cultured cells expressing hNPR-C. FIGS. 4A and 4B demonstrate the resistance to inactivation of a receptor specffic ANF variant (hANF(1-28) R3D, G9T, R11S, M12L, R145, G16R) in a culture of cells expressing hNPR-A alone or in a co-culture of cells expressing both hNPR-A and hNPR-C. Measurement of cGMP production in 293 cells expressing hNPR-A demonstrates that wild-type ANF stimulates guanyl cyclase activity. When a ten-fold excess of 293 cells that highly express hNPR-C (~$10^6$ "C" receptors/cell) is added, the activity of wild-type ANF is greatly reduced ($EC_{50}$ is about 25-fold higher, see FIG. 4A). However, when this experiment is repeated with the receptor specific variant, complete resistance to inactivation is observed (FIG. 4B). Comparison of FIG. 4A and 4B also demonstrates that the receptor specific variant is equipotent to wild-type ANP in stimulating cGMP production from hNPR-A. Based on these findings and the literature reports that hNPR-C mediated clearance accounts for 70–80% of in vivo ANF clearance, the variants of this invention are believed to have superior pharmaceutical utility.

Figure 5:
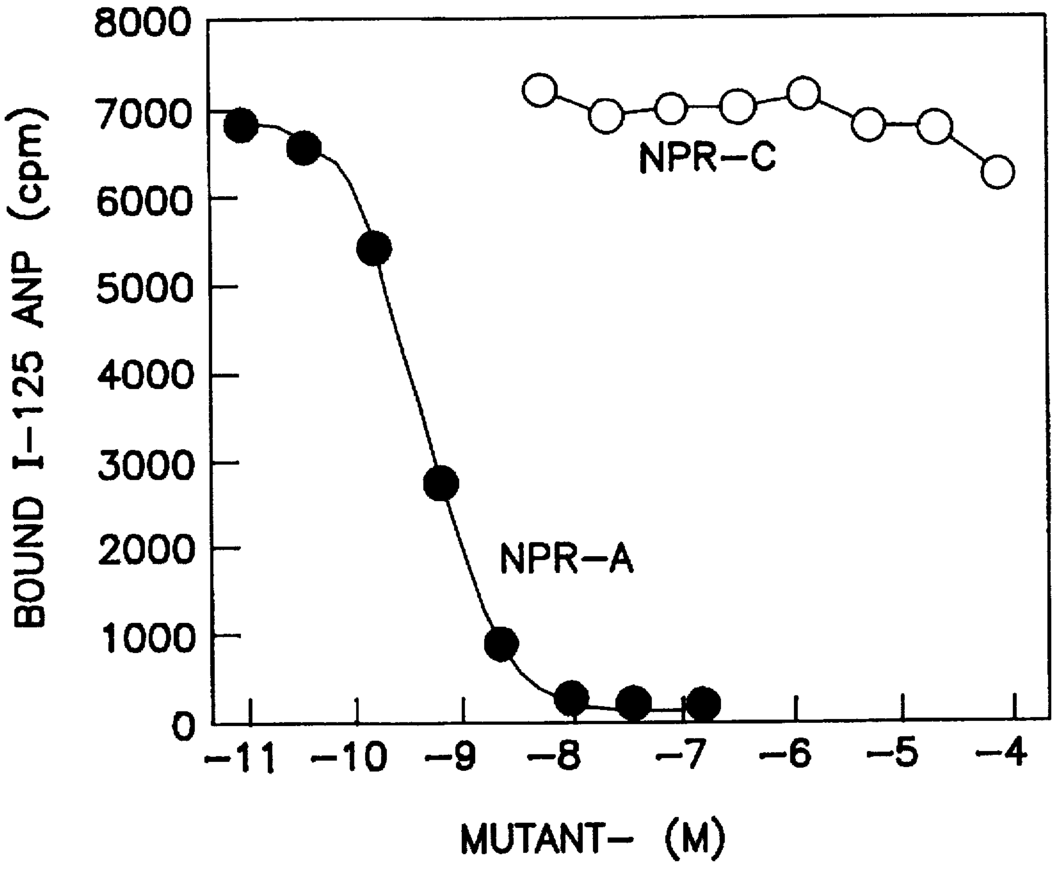
FIG. 5. Binding specificity of mutant hANF(1–28) R3D, G9T, R11S, M12L, R14S, G16R.

From an analysis of a large number of variants, the single naturally occurring amino acid substitution that produced the greatest receptor specificity was G16R. This substitution had a negligible effect on NPR-A binding but reduced NPR-C affinity about 150-fold. FIG. 5 shows the binding specificity for a typical variant containing the G16R substitution. Specifically, variant hANF(1-28) R3D, G9T, R11S, M12L, R14S, G16R competitively displaced bound $I^{125}$ labeled wild-type ANF from hNPR-A but showed no measurable affinity for the clearance receptor hNPR-C. Other receptor specific variants are presented in Table I below.

TABLE I

| ANF Variant No. | Structure* (see Formula I) X | AA$_9$ | AA$_{10}$ | AA$_{11}$ | AA$_{12}$ | AA$_{14}$ | AA$_{16}$ | AA$_{18}$ | Binding Affinity $IC_{50}$ (pM) hNPR-A | hNPR-C |
|---|---|---|---|---|---|---|---|---|---|---|
| 14 (wild type) | | — | — | — | — | — | — | — | 110 | 230 |
| 23 | TAPR | — | — | — | I | — | R | — | 44 | 4193 |
| 24 | | — | — | — | I | — | R | — | 57 | 5639 |
| 25 | | — | — | — | I | S | R | — | 56 | 3305 |
| 27 | | T | — | S | — | — | R | — | 57 | 1,000,000 |
| 31 | | t | — | S | — | — | R | P | 52 | 3,213,100 |
| 32 | | E | R | P | I | — | R | — | — | — |
| 50 | | T | — | s | — | — | — | — | 570 | 251,000 |
| 51 | | E | R | P | — | — | — | — | 4,550 | 32,200 |
| 60 | | — | K | S | — | — | — | — | 112 | 5980 |
| 70[a] | | T | — | S | L | S | R | C*—C* | 3,300 | — |
| 74[b] | | T | — | S | I | — | R | — | 29,400 | 10,000,000 |
| 75[c] | | T | — | S | I | — | R | — | 2,075 | 2,000,000 |
| 76[d] | TAPR | T | — | S | I | — | — | — | 8.9 | 10,000,000 |
| 78 | | a | — | S | I | — | R | — | 57 | 8641 |

TABLE I-continued

| ANF Variant No. | Structure* (see Formula I) X | AA$_9$ | AA$_{10}$ | AA$_{11}$ | AA$_{12}$ | AA$_{14}$ | AA$_{16}$ | AA$_{18}$ | Binding Affinity IC$_{50}$ (pM) hNPR-A | hNPR-C |
|---|---|---|---|---|---|---|---|---|---|---|
| 79[e] | | T | — | S | I | — | R | — | 2.4 | 1,481,300 |
| 80[f] | | T | — | S | I | — | R | — | 423 | 738,640 |
| 81[g] | | T | — | S | I | — | R | — | 1400 | 3,864,200 |
| 82[h] | | T | — | S | I | — | R | — | 93 | 3,006,000 |
| 83[i] | | T | — | S | I | — | R | — | 16 | 3,440,000 |
| 84[j] | | T | — | S | I | — | R | — | 21 | 19,000,000 |
| 90[k] | | a | — | D | I | — | R | — | 1,200 | 6,140,000 |
| 100-1[l] | | T | — | S | I | — | R | — | 187 | 3,230,000 |
| urod. | TAPR | — | — | — | — | — | — | — | 25 | 25 |

*A blank (—) in the table indicates no deviation from the wild type sequence.
C*—C* homocys$^{18}$-homocys$^{28}$ disulfide bridges.
[a]ANF70 additionally contains a R3D substitution.
[b]D-Ser inserted between residue AA$_7$ and AA$_8$.
[c]D-Ala inserted between residue AA$_7$ and AA$_8$.
[d]Also contains G20R substitution.
[e]Cha inserted between residue AA$_7$ and AA$_8$.
[f]des(AA$_1$—AA$_6$), C7Mpa.
[g]des(AA$_1$—AA$_6$), C7Mpa.
[h]Also contains C(N—MeCys).
[i]Also contains F8(N—MePhe).
[j]Also contains C78F8 replaced with C($\psi$CH$_2$NH)F.
[k]a is D-Ala.
[l]Also contains F8(Phg).

Figure 6:
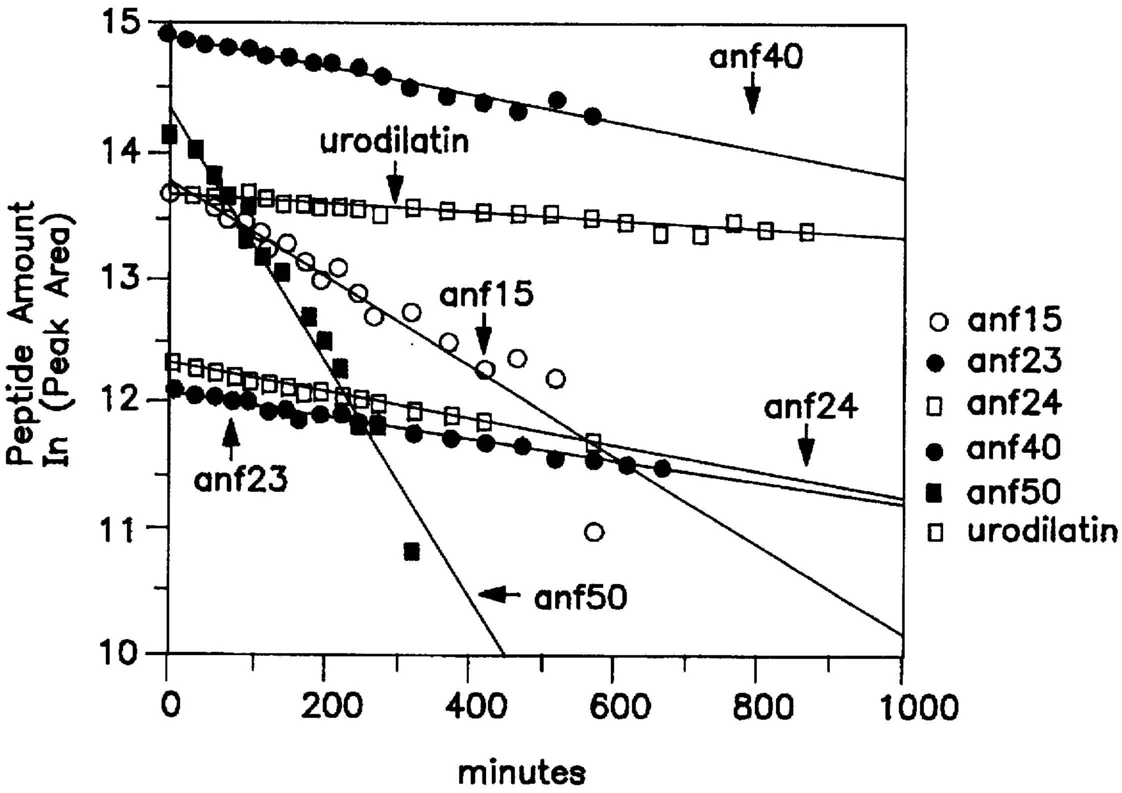
FIG. 6. Degradation of ANF variants (0.5 mg/ml) by endopeptidase 11.24 (NEP) (0.225 mg/ml). Peptides having the following sequences were assayed as provided in Example 22.

Inhibition of cleavage of ANF variants by human NEP (hNEP) is demonstrated in FIGS. 6, 7 and 8. Human Endopeptidase 24.11 inactivates ANF by cleaving the sissile Cys$^7$-Phe$^8$ amide bond. Assay conditions for measurement of the half-life of various ANF variants is described in Example 22. Half-Lives for variants can be found in the legends (Brief Description of Drawings) to FIGS. 6, 7 and 8.

E. Utility and Administration

Compounds of the present invention have natriuretic, diuretic and vasorelaxant activity and may inhibit the release of aldosterone and renin. Thus, these compounds, find use as therapeutic agents in the treatment of various pathological conditions associated with water or electrolyte imbalance and hypertension, especially renovascular hypertension. Such conditions include, for example, congestive heart failure (CHF), nephrotic syndrome and hepatic cirrhosis, pulmonary disease, and renal failure due to ineffective renal perfusion or reduced glomerulax filtration rate.

The present invention also provides compositions containing an effective amount of compounds of the present invention, including the nontoxic addition salts, amides and esters thereof, which may, alone, serve to provide the above-recited therapeutic benefits. Such compositions can be provided together with physiologically tolerable liquid, gel or solid diluents, adjuvants and excipients.

The compounds and compositions can be administered to humans in a manner similar to other therapeutic agents. The dosage to be administered will depend on the usual factors including; age, weight, sex, condition of the patient and route of administration. In general, the dosage required for therapeutic efficacy will range from about 0.01 to 1000 μg/kg, more usually 0.1 to 25 μg/kg of the host body weight. Alternatively, dosages within these ranges can be administered by constant infusion over an extended period of time until the desired therapeutic benefits have been obtained.

Typically, such compositions are prepared as injectable liquid solutions or suspensions. Compositions may also be emulsified. The active ingredient is often mixed with diluents or excipients which are physiologically tolerable and compatible with the active ingredient. Suitable diluents and excipients are, for example, water saline, dextrose, glycerol, or the like, and combinations thereof. In addition, if desired the compositions may contain minor amounts of auxiliary substances such as wetting or emulsifying agents, stabilizing or pH-buffering agents, and the like. For a more detailed description of the foregoing see a standard pharmaceutical text such as *Remington's Pharmaceutical Sciences,* Mack Publishing Co. Easton, Pa. (1970).

The compositions of this invention are conventionally administered parenterally by injection, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% if active ingredient, preferably 25%–70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropyl amine, 2-ethylamino ethanol, histidine, procaine, and the like.

In addition to the compounds of the present invention which display natriuretic, diuretic or vasorelaxant activity, compounds of the present invention can also be employed as intermediates in the synthesis of such useful compounds. Alternatively, by appropriate selection, compounds of the present invention whose activity levels are reduced or eliminated entirely can serve to modulate the activity of other diuretic, natriuretic or vasorelaxant compounds, including compounds outside the scope of the present invention, by, for example, binding to alternate receptors, stimulating receptor turnover, or providing alternate substrates for degradative enzyme of receptor activity and thus inhibiting these enzymes or receptors. When employed in this manner, such compounds can be delivered as admixtures with other active compounds or can be delivered separately, for example, in their own carriers.

EXAMPLES

In the following Examples, amino acids are described by the standard three letter amino acid code when referring to intermediates and final products. The linear peptides and intermediates described herein are prepared by the solid phase method of peptide synthesis (R. Merrifield, *J. Am. Chem. Soc.* 1964, 85, 2149 and M. Bodansky, "Principles of Peptide Synthesis," Springer-Verlag, 1984). Abbreviations used are as follows: tert-butyloxycarbonyl (Boc); p-toluenesulfonyl (Tos); 4-methylbenzyl (MeBzl); benzyl (Bzl); 2-bromobenzyloxycarbonyl (Br-Z); cyclohexyl ester (Ochex); 4-methoxylbenzyl (MeOBzl), 2-chlorobenzyloxycarbonyl (Cl-Z); hydrogen fluoride (HF); benzotriazolyloxytris(dimethylamino) phosphoniumhexafluorophosphate (BOP); methylene chloride (DCM); trifluoroacetic acid (TFA); and dimethylacetamide (DMA).

Peptides were assembled using an Applied Biosystems 430A automated peptide synthesizer. Protected amino acids were obtained from various vendors. Side chain protection was Asp (Ochex), Cys (MeOBzl), Arg (Tos), Ser(Bzl), Thr (Bzl), Lys (Cl-Z), and Tyr (Br-Z).

EXAMPLE 1

Thr-Ala-Pro-Arg-Ser-Leu-Arg-Arg-Ser-Ser-Cys-Phe-Gly-Gly-Arg-Ile-Asp-Arg-Ile-Arg-Ala- Gln-Ser-Gly-Leu-Gly-Cys-Asn-Ser-Phe-Arg-Tyr (SEQ ID NO: 5), $Cys^7$-$Cys^{23}$ disulfide (ANF23)

The peptide was assembled on 0.7 g (1.0 mmol) of Boc-Tyr(Br-Z) PAM resin (Applied Biosystems). The coupling protocols were those recommended by Applied Biosystems and DMA was used instead of DMF as solvent. After chain assembly the N-terminal Boc group was removed using TFA. The peptide resin was then washed with dichloromethane followed by methanol and then dried under vacuum. The peptide was then deprotected and removed from the resin by stirring the peptide-resin in 20 ml of a mixture of HF (92.5%), anisole (5%) and ethylmethylsulfide (2.5%) for 1 hr at 0 degrees. The HF was then removed in vacuo and the resin washed with ether. The resin was washed with 10% acetic acid in water, acetonitrile, water, and the filtrate was recovered and lyophilized. The crude linear peptide (300 mg) was dissolved in 10 L of distilled water with the pH adjusted to 7.4–7.6 with concentrated ammonium hydroxide. The cyclization is begun immediately by adding 0.003 M $K_3[Fe(CN)_6]$ (1 g dissolved in 100 mL of distilled water) dropwise (ca. 1 drop/10 sec.) with vigorous stirring. Addition of the iron solution is halted when a bright yellow color persists, and the reaction mixture is stirred for an addition 4 to 5 h. The pH of the cyclized solution is adjusted to 4.5 with HOAc.

Bio Rex 70 cation exchange resin, 200–400 mesh in the $Na^+$ form is washed with 1N HCl and then with distilled water. Approximately 110 g of this resin is added to the cyclized peptide solution and stirred overnight. The resin is filtered, washed exhaustively with distilled water, and slurry packed into a column. The peptide is eluted using 70% aqueous HOAc, identified by TLC (ninhydrin visualization) and lyophilized. The peptide was dissolved in 0.1% TFA in water, loaded onto a 2.5 cm×50 cm C-18 reversed phase column (15 micron, 300A) and eluted with a shallow gradient of increasing acetonitrile. The elution conditions consisted of a 10% to 50% acetonitrile (containing 0.1% TFA) gradient at 0.5% $min.^{-1}$. The aqueous phase was 0.1% TFA in water. Product containing fractions were then lyophilized to afford the pure title peptide. Electrospray ionization: Electrospray ionization: Calc. M+H=3586.2; found 3586.3. HPLC $t_R$=29 min.

Following the procedure in Example 1, the compounds of Examples 2–9 were analogously prepared.

EXAMPLE 2

Ser-Leu-Arg-Arg-Ser-Ser-Cys-Phe-Gly-Gly-Arg-Ile-Asp-Arg-Ile-Arg-Ala-Gln-Ser-Gly-Leu- Gly-Cys-Asn-Ser-Phe-Arg-Tyr (SEQ ID NO: 6), $Cys^7$-$Cys^{23}$ disulfide (ANF24)

Electrospray ionization: Calc. M+H=3162; found 3161.3. HPLC $t_R$=31 min.

EXAMPLE 3

Ser-Leu-Arg-Arg-Ser-Ser-Cys-Phe-Thr-Gly-Ser-Ile-Asp-Arg-Ile-Arg-Ala-Gln-Ser-Gly-Leu- Gly-Cys-Asn-Ser-Phe-Arg-Tyr (SEQ ID NO: 11), $Cys^7$-$Cys^{23}$ disulfide (ANF27)

Electrospray ionization: Calc. M+H=3135.3; found 3135.6. HPLC $t_R$=31 min.

EXAMPLE 4

Ser-Leu-Arg-Arg-Ser-Ser-Cys-Phe-Arg-Gly-Asp-Ile-Asp-Arg-Ile-Arg-Ala-Gln-Ser-Gly-Leu- Gly-Cys-Asn-Ser-Phe-Arg-Tyr (SEQ ID NO: 12), $Cys^7$-$Cys^{23}$ disulfide (ANF 28)

Electrospray ionization: Calc. M+H=3218.7; found 3219.4. HPLC $t_R$=30 min.

EXAMPLE 5

Ser-Leu-Arg-Arg-Ser-Ser-Cys-Phe-Thr-Gly-Ser-Ile-Asp-Arg-Ile-Arg-Ala-Pro-Ser-Gly-Leu- Gly-Cys-Asn-Ser-Phe-Arg-Tyr (SEQ ID NO: 13), $Cys^7$-$Cys^{23}$ disulfide (ANF31)

Electrospray ionization: Calc. M+H=3104.8; found 3104.6. HPLC $t_R$=30 min.

EXAMPLE 6

Ser-Leu-Arg-Arg-Ser-Ser-Cys-Phe-Thr-Gly-Ser-Met-Asp-Arg-Ile-Gly-Ala-Gln-Ser-Gly-Leu- Gly-Cys-Asn-Ser-Phe-Arg-Tyr (SEQ ID NO: 8), $Cys^7$-$Cys^{23}$ disulfide (ANF50)

Electrospray ionization: Calc. M+H=3054.4; found 3054.0. HPLC $t_R$=30 min.

EXAMPLE 7

Ser-Leu-Arg-Arg-Ser-Ser-Cys-Phe-Glu-Arg-Pro-Met-Asp-Arg-Ile-Gly-Ala-Gln-Ser-Gly-Leu- Gly-Cys-Asn-Ser-Phe-Arg-Tyr (SEQ ID NO: 25), $Cys^7$-$Cys^{23}$ disulfide (ANF51)

Electrospray ionization: Calc. M+H=3190.8; found 3191.9. HPLC $t_R$=31 min.

EXAMPLE 8

Ser-Leu-Arg-Arg-Ser-Ser-Cys-Phe-Gly-Lys-Ser-Met-Asp-Arg-Ile-Gly-Ala-Gln-Ser-Gly-Leu- Gly-Cys-Asn-Ser-Phe-Arg-Tyr (SEQ ID NO: 14), $Cys^7$-$Cys^{23}$ disulfide (ANF60)

Electrospray ionization: Calc. M+H=3082.4; found 3082.3. HPLC $t_R$=28 min..

EXAMPLE 9

Ser-Leu-Asp-Arg-Ser-Ser-Cys-Phe-Thr-Gly-Ser-Leu-Asp-Ser-Ile-Arg-Ala-homocysteine-Ser- Gly-Leu-Gly-Cys-Asn-Ser-Phe-Arg-homocysteine (SEQ ID NO: 37) $Cys^7$-$Cys^{23}$ disulfide, $homocysteine^{18}$-$homocysteine^{28}$ disulfide (ANF70)

The following standard manual peptide synthesis protocol was employed in the construction of this multiple disulfide variant ("tie-down" variant):

(1) Wash 3× with dichloromethane (DCM)

(2) Treat for 1 min. with 50:50 TFA/DCM (3) Treat for 20 min. with 50:50 TFA/DCM (4) Wash 3× with DCM (5) Treat for 1 min. with 5% (v/v) DIPEA/DCM.

(6) Treat for 5 min. with 5% (v/v) DIPEA/DCM.

(7) Wash 4× with DCM.

(8) Wash 1× with N-methyl-2-pyrroldinone (NMP).

(9) Add 5 equivalents of the Boc-protected amino acid 5 equivalents of diisopropylcarbodiimide (DIPC) and 5 equivalents of hydroxybenzotriazole (HOBT) in 50:50 DCM/NMP.

(10) Wash 1× with NMP.

(11) Wash 3× with DCM.

(12) Test by ninhydrin reaction according to Kaiser et al., *Anal. Biochem.* 1970, 34, 595. If the coupling reaction is incomplete, repeat steps 5–12.

The peptide was synthesized manually, starting with 1.5 g (0.92 mmol) of Boc-homocysteine (MeBzI) Merrifield resin. The peptide was synthesized using standard t-Boc chemistry protocol. $Cysteine^7$ and $cysteine^{23}$ side chains were protected as acetamidomethyl (Acm) thioethers while $homocysteine^{18}$ and $homocysteine^{28}$ side chain were protected as methyl benzyl (MeBzl) thioethers. The side chain carboxylate of $Asp^{13}$ was protected as the benzyl ester; the caxboxylate side chain of $Asp^3$ was protected as a cyclohexyl ester. After peptide chain assembly, the N-terminal Boc group was removed using TFA. The peptide resin was then washed with dichloromethane followed by ethanol and dried under vacuum. The peptide was then deprotected and removed from the resin by stirring the peptide resin in 40 mL of a mixture of HF (92.5%), anisole (5%) and ethyl methyl sulfide (2.5%) for one hour in an ice bath. The HF was then removed in vacuo and resin was washed with ether. The peptide was extracted from resin by washing with 10% acetic acid in water followed by water. The filtrate was pooled and lyophilized. The crude linear peptide (400 mg) was dissolved in 800 ml of water with pH adjusted to 8.0 with ammonium hydroxide. The solution was stirred for 72 hours at room temperature after which solution was acidified with TFA, filtered and loaded onto a 1.0 cm×50 cm C-18 reversed phase column (15 micron, 300 A). The peptide was eluted with a shallow gradient of 10% to 50% acetonitrile (containing 0.1% TFA) with increasing acetonitrile at 0.5%/min. The aqueous phase was 0.1% TFA in water. The intermediate product ($homocys^{18}$, $homocys^{28}$ disulfide) fractious were lyophilized. Electron spray ionization: calc. M+H=3110.3, found=3110.0. HPLC tR=38 min. The intermediate product ($homocys^{18}$, $homocys^{28}$ disulfide—20 mg) was dissolved in 40 mL of acetic acid: water (80:20). A solution of iodine was prepared in glacial acetic acid and added dropwise to peptide containing solution over a period of time until brownish yellow color persisted. The mixture was stirred overnight (20 hr). Small amounts of zinc dust were added to the mixture the next day until solution became colorless. The solution was filtered, diluted with water and lyophilized. The lyophilized crude peptide was dissolved in 50 ml of 5% acetonitrile in water, filtered and loaded onto a 1×50 cm Vydac (18 column—15–20 micron, 300 A) for HPLC purification.

The peptide was eluted with a shallow gradient of 17% to 32% acetonitrile (containing 0.1% TFA) with increasing acetordtrile at 0.25% $min.^{-1}$. The product containing fractions were lyophilized: Electrospray ionization: Calc. M+H=2966.2; found 2966.69.

EXAMPLE 10

Boc-Ile-(Cy)Asp-(Tos)Arg-Ile-Tos)Arg-Ala-Gln-(Bz)Ser-Gly-Leu-Gly-(pMB)Cys-Asn- (Bz)Ser-Phe-Tos)Arg-(2-Br-CBZ)Tyr-PAM-resin Boc-(Br-cbz)Tyr-PAM resin(25 gm, substitution of 0.51 mmoles/gm) was bought from Bachem Inc., Torrance, Calif., while rest of the BOC-amino acid derivatives were from Star Biochemicals, Torrance, Calif. The side-chain protection for arginine, cysteine and serine derivatves were chosen as tosyl(Tos), p-methyl benzyl(pMB) and benzyl(Bz) respectively.

| | |
|---|---|
| Wash volumes: | 10 ml/gm resin |
| Pre-wash | $CH_2Cl_2$, 3 times, 1 min. mix each time |
| De-protection: | TFA/$CH_2Cl_2$ (1:1), 1 time, 1 min. mix |
| | TFA/CH2Cl2 (1:1), 1 time, 30 min. mix |
| Wash | $CH_2Cl_2$, 4 times, 1 min. mix each time |

-continued

| | |
|---|---|
| Neutralization | 5% DIEA/$CH_2Cl_2$, 3 times, 1 min. mix each time |
| Wash | $CH_2Cl_2$, 4 times, 1 min. mix each time |

Kaiser test was performed on a few beads to note the reference bead color to compare it the test color after the coupling.

Coupling Protocol

Four molar excess amount of the amino acid derivatives were used in all the couplings for each mole of the tyrosine PAM resin. Diisopropyl carbodiimide (DIPC) and N-hydroxy benzotriazole (HOBT) were used as coupling reagents in similar molar excess as the amino acids for all the residues except alanine. Alanine was coupled with four molar excess of benzotriazol-1-yloxy-tris(dimethylamino) phosphonium hexafluorophosphate(BOP) and HOBT and six molar excess of N-methyl morpholine(NMM) for one hour. The DIPC and HOBT couplings were generally done for two hours. The completion of the coupling was inferred by a negative Kaiser test. Last five residues (residue nos. 1 through 5) had to be double coupled using BOP/HOBT, while the rest were coupled in the first attempt. For the second coupling only half the amounts were used for the residues 1,2,3 and 5, while for the 4th residue same amounts of the amino acids and reagents were used.

At the end of the synthesis the resin was deprotected, washed thoroughly with $CH_2Cl_2$, $CH_2Cl_2$/Ethanol (1:1) and dried in a desiccator. The final weight of the resin peptide was 45 gm. (Theo. 50.9 gm.). Procedures analogous to those used in example 1 were used to complete the synthesis of the following peptides.

EXAMPLE 11

Ser-Leu-Arg-Arg-Ser-Ser-Cys-(D-Ser)-Phe-Thr-Gly-Ser-Ile-Asp-Arg-Ile-Arg-Ala-Gln-Ser- Gly-Leu-Gly-Cys-Asn-Ser-Phe-Arg-Tyr (SEQ ID NO: 27), $Cys^7$-$Cys^{24}$ disulfide (ANF74)

Electrospray ionization: Calc. M+H=3223.5; found 3222.9. HPLC $t_R$=30 min..

EXAMPLE 12

Ser-Leu-Arg-Arg-Ser-Ser-Cys-(D-Ala)-Phe-Thr-Gly-Ser-Ile-Asp-Arg-Ile-Arg-Ala-Gln-Ser- Gly-Leu-Gly-Cys-Asn-Ser-Phe-Arg-Tyr (SEQ ID NO: 28), $Cys^7$-$Cys^{24}$ disulfide (ANF75)

Electrospray ionization: Calc. M+H=3207.5; found 3207.0. HPLC $t_R$=33 min..

EXAMPLE 13

Thr-Ala-Pro-Arg-Ser-Leu-Arg-Arg-Ser-Ser-Cys-Phe-Thr-Gly-Ser-Ile-Asp-Arg-Ile-Arg-Ala- Gln-Ser-Gly-Leu-Gly-Cys-Asn-Ser-Phe-Arg-Tyr (SEQ ID NO: 15), $Cys^{11}$-$Cys^{27}$ disulfide (ANF76)

Electrospray ionization: Calc. M+H=3559.7; found 33561.0. HPLC $t_R$=28 min..

EXAMPLE 14

Ser-Leu-Arg-Arg-Ser-Ser-Cys-Cha-Thr-Gly-Ser-Ile-Asp-Arg-Ile-Arg-Ala-Gln-Ser-Gly-Leu- Gly-Cys-Asn-Ser-Phe-Arg-Tyr (SEQ ID NO: 16), $Cys^7$-$Cys^{23}$ disulfide (where Cha=1-cyclohexylalanine)

(ANF79)

Electrospray ionization: Calc. M+H=3141.8; found 3142.2. HPLC $t_R$=35 min..

EXAMPLE 15

Mpa-Phe-(D-Thr)-Gly-Ser-Ile-Asp-Arg-Ile-Arg-Ala-Gln-Ser-Gly-Leu-Gly-Cys-Asn-Ser-Phe- Arg-Tyr (SEQ ID NO: 30), $Mpa^1$-$Cys^{17}$ disulfide (Mpa= mercaptopropionic acid).

(ANF80)

Electrospray ionization: Calc. M+H=2433.2; found 2434.6. HPLC $t_R$=38 min..

EXAMPLE 16

Mpa-Phe-(D-Ala)-Gly-Ser-Ile-Asp-Arg-Ile-Arg-Ala-Gln-Ser-Gly-Leu-Gly-Cys-Asn-Ser-Phe- Arg-Tyr (SEQ ID NO: 31), $Mpa^1$-$Cys^{17}$ disulfide (Mpa= mercaptopropionic acid)

(ANF81)

Electrospray ionization: Calc. M+H=2403.2; found 2404.3. HPLC $t_R$=36 min..

EXAMPLE 17

Ser-Leu-Arg-Arg-Ser-Ser-(N-Me-1-Cys)-Phe-Thr-Gly-Ser-Ile-Asp-Arg-Ile-Arg-Ala-Gln-Ser- Gly-Leu-Gly-Cys-Asn-Ser-Phe-Axg-Tyr (SEQ ID NO: 17), $Cys^7$-$Cys^{23}$ disulfide (ANF82)

Electrospray ionization: Calc. M+H=3156.5; found 33150.0. HPLC $t_R$=29 min..

EXAMPLE 18

Ser-Leu-Arg-Arg-Ser-Ser-Cys-(N-Me-1-Phe)-Thr-Gly-Ser-Ile-Asp-Arg-Ile-Arg-Ala-Gln-Ser- Gly-Leu-Gly-Cys-Asn-Ser-Phe-Arg-Tyr (SEQ ID NO: 18), $Cys^7$-$Cys^{23}$ disulfide (ANF83)

Electrospray ionization: Calc. M+H=3148.5; found 3149.6. HPLC $t_R$=30 min..

EXAMPLE 19

Ser-Leu-Arg-Arg-Ser-Ser-Cys-Phe-(D-Ala)-Gly-Asp-Ile-Asp-Arg-Ile-Arg-Ala-Gln-Ser-Gly- Leu-Gly-Cys-Asn-Ser-Phe-Arg-Tyr (SEQ ID NO: 34), $Cys^7$-$Cys^{23}$ disulfide (ANF 90)

Electrospray ionization: Calc. M+H=3132.5; found 3133.7. HPLC $t_R$=33 min..

EXAMPLE 20

Ser-Leu-Arg-Arg-Ser-Ser-Cys-Phg-Thr-Gly-Ser-Ile-Asp-Arg-Ile-Arg-Ala-Gln-Ser-Gly-Leu- Gly-Cys-Asn-Ser-Phe-Arg-Tyr (SEQ ID NO: 35), $Cys^7$-$Cys^{23}$ disulfide (Phg is d and 1 phenyl glycine)

(ANF 100-1)

Electrospray ionization: Calc. M+H=3120.6; found 3121.8. HPLC $t_R$=30 min..

EXAMPLE 21

Ser-Leu-Arg-Arg-Ser-Ser-Cys(ψ$CH_2$NH)Phe-Thr-Gly-Ser-Ile-Asp-Arg-Ile-Arg-Ala-Gln-Ser- Gly-Leu-Gly-Cys-Asn-Ser-Phe-Arg-Tyr (SEQ ID NO: 33), $Cys^7$-$Cys^{22}$ disulfide (ANF 84)

C(ψ$CH_2$NH)F represents the peptide segment derived from the amino acid below:

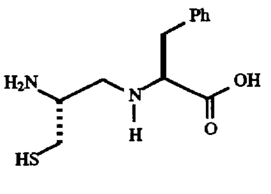

For the synthesis of the titled compound, 1.53 g of the resin pepride containing residues 12–27 was used. The next four residues (Phe-"8", Thr-9, Gly-10, Ser-11) were coupled manually using the standard protocols described above (ca. 4 eq reagent, BOP/HOBT/NMM couplings; repeat couplings, when necessary, with 3 eq reagent and DIPC) and the N-terminal t-Boc protecting group was removed using the TFA deblock procedure. N-Boc, S-4-methylbenzyl cysteinal (2.86 g of crude material prepared as described below) was added to the resin peptide (after the standard deblock, neutralization and washes) and 1.0 g of $NaCNBH_3$ in AcOH/DMF (1% v/v) at room temperature for 18 h. The resin was washed twice with AcOH/DMF (1% v/v), once with DMA, and twice with $CH_2Cl_2$. The N-terminal t-Boc protecting group was removed and the synthesis was continued using the standard protocol.

N-Boc S-4-Methylbenzyl Cysteinal. N-Boc-S-(4-methylbenzyl) L-cysteine (49.64 g, 153 mmol), BOP (67 g, 151 mmol), HOBT (22 g, 163 mmol), and 400 mL of $CH_2Cl_2$ where combined in a 1 L round-bottomed flask equipped with a magnetic stirring bar and cooled in a ice bath. N-Methylmorpholine (NMM, 18 mL, 16.56 g, 164 mmol) was added dropwise to the stirring solution over a 5 min. period. After completion of the addition, the reaction mixture was removed from the cooling bath and stirred for a 15 min period at room temperalure. N,O-dimethylhydroxylamine hydrochloride (19 g, 195 mmol) was added as a solid to the stirring solution followed by the dropwise addition of 35 mL (25.97 g, 200 mmol) of diisopropyl ethyl amine. The resulting solution was stirred overnight, partitioned between $CH_2Cl_2$ and 10% (w/v) aqueous $K_2CO_3$, followed by 10% (w/v) aqueous citric acid and then brine. After drying the organic extracts over anhydrous sodium sulfate, the reaction mixture was filter and concentrated under reduced pressure. The crude material was chromatographed using 1 kg of silica gel (Merck, 230–400 mesh) using 2:1 hexanes/ethyl acetate as eluent to provide 43.95 g (119 mmol, 79%) of N-Boc-S-(4-methylbenzyl) L-cysteine N,O-methoxymethylamide as a viscous, clear oil.

To a solution of 11.54 g (32.6 mmol) of N-Boc-S-(4-methylbenzyl) L-cysteine N,O-methoxymethylamide in 65 mL of anhydrous $Et_2O$ in a 250 mL oven-dried, round-bottomed flask equipped with a magnetic stirring bar and a $N_2$ inlet and cooled to −78° C. in a dry ice/acetone bath was added 35 mL (35 mmol) of an 1.0M solution of $LiAlH_4$ in THF (Aldrich) by syringe over a period of 20 minutes (caution: gas is evolved during the addition). After stirring for a 15 min period at −78° C., the reaction mixture is removed from the cooling bath and the reaction mixture is allowed to warm to 0° C. (takes ca 30–60 min) and kept at this temperature for an additional 30–60 min using an ice bath. Keeping the reaction flask in the cooling bath, a solution of 9 g of $KHSO_4$ in 180 mL DI water is slowly added over approximately 20 minutes while stirring (caution: vigorous gas evolution and exotherm. A dry ice/acetone bath was used when necessary to keep reaction temperature at ca. 10° C.). Working quickly, the reaction flask is removed from the dry ice cooling bath and the reaction slurry is allowed to warm to room temperature. Additional $Et_2O$ is added and the mixture is diluted with water. The resulting suspension is vacuum filtered through a plug of celite. The organic layer were separated and the aqueous layers were extracted with ether (3×100 mL) and the combined organic layers were washed 2×50 mL of cold 0.3 N HCl, 1×50 mL of a saturated aqueous solution of $NaHCO_3$, and 50 mL of brine, dried using anhydrous $MgSO_4$, filtered, and concentrated using a rotary evaporator with a room temperature water bath to give 8.57 g of crude aldehyde. NMR is used to assess the purity of the aldehyde and ca. ⅓ of the aldehyde was used directly in the reductive alkylation without further purification (essentially as in Feherenz et al., *Synthesis,* 676–678 [1983]). Electrospray ionization: Calc. M+H=3119.5; found 3121.7. HPLC $t_R$=30 min..

EXAMPLE 22

Inhibition of Cleavage of ANF Variants by Human NEP (hNEP)

Human endopeptidase 24.11 inactivates ANF by cleaving the sissile $Cys^7$-$Phe^8$ amide bond. The half-life of various ANF variants was measured according to the following procedure.

ANF Solution: An accurately weighed amount of ANF or variant thereof was diluted with HEPES buffer (5 ml of 1M HEPES Buffer and 0.1 ml of Tween 20 diluted to a 100 ml volume with DI water) to make a 0.5 mg/ml solution.

hNEP/HEPES Solution: 75 μl of a 1 mg/ml solution of hNEP (see U.S. Pat. No. 4,960,700) is dissolved in 992.5 μl of HEPES buffer (as described above) and vortex mixed. The resulting mixture is stored in a silylated Eppendorf tube and periodically checked for activity against an ANF peptide standard.

Assay conditions: 150 μl of an ANF solution in the HEPES buffer is diluted with 820 μl HEPES buffer and vortex mixed (1 sec). Careful note of the time is taken as 30 μl of the hNEP/HEPES solution is added and the solution is vortex mixed for 1 sec. and analyzed by periodic removal of constant volume aliquots by the HPLC autosampler. A 2.5 cm×50 cm, C-18 reversed-phase column (15 micron, 300Å]) was used and elution was achieved by using a shallow gradient of increasing acetonitrile. The elution conditions consisted of a 10% to 50% acetonitrile (containing 0.1% TFA) gradient at 0.5% $min.^{-1}$. The aqueous phase was 0.1% TFA in water. The peak area of the ANP peptide is recorded at these periodic intervals and a half-life is determined from these values.

In the recombinant methods described below in Examples 23–25 the following materials and methods were used. The Nugel P-RP reverse phase resin was purchased from Separation Industries and the Vydac C18 and Mono S columns from Pharmacia LKB Biotechnology, Inc. Oligonucleotides were synthesized using hydrogen phosphonate chemistry (Froehler, B. C. et al., *Nucleic Acids Res.* 14:5399–5407

[1986]) and purified by polyacrylamide gel electrophoresis (PAGE). *E. coli* strain XL1-Blue MRF' was purchased from Stratagene. Restriction enzymes were from New England Biolabs. All other reagents were obtained were of the highest grade commercially available.

EXAMPLE 23

Construction of the ANF Expression Vector

All DNA manipulations were performed according to standard procedures unless otherwise indicated (Sambrook et al., supra). The ANF gene was assembled from synthetic oligonucleotides designed to code for the published sequence of the ANF and code for the restriction sites Nsi I and Apa at the 5' and 3' ends of the gene, respectively. Three sense strand oligonucleotides and 3 overlapping anti-sense strand oligonudeotides were synthesized. The sequence of the sense strands were;

5'-TCTCTGCGTAGATCTAGCTGCTTCGGCGGCCGCATG (SEQ ID NO: 38),

5'-GATCGTATCGGAGCTCAGAGCGGTCTCGGGTGCAA (SEQ ID NO: 39) and

5'-CAGCTTCCGTTACGTAGGCGGGCC (SEQ ID NO: 40).

The sequence of the anti-sense strands were;

5'-CAGCTAGATCTACGCAGAGATGCA (SEQ ID NO: 41),

5'-TCTGAGCTCCGATACGATCCATGCGGCCGCCGAAG (SEQ ID NO: 42) and

5'-CGCCTACGTAACGGAAGCTGTTGCACCCGAGACCGC (SEQ ID NO: 43).

These oligonucleotides were phosphorylated, ligated together and the ligation product digested with Nsi I and Apa I after heat inactivation of the ligase. The digest was then electrophoresed on a 5% polyacrylamide gel in 89 mM Tris-borate, 1 mM EDTA, pH 7.9, the gel was stained with ethidium bromide, and a band of approximately 95 base pairs was excised and the DNA electro-eluted. The ANF expression vector pB1325 was created by ligating the fragment obtained from the oligonucleotide assembly into the large vector fragment of Nsi I and Apa I digested pS0132. After ligation *E coli* XL-1 cells were transformed with the mixture and ampicillin resistent colonies were selected. DNA was subsequently isolated from a number of these colonies and subjected to dideoxy sequencing (Sanger, F., Nicklen, S., and A. R. Coulsen, *Proc. Natl, Acad. Sci. U.S.A.* 74:5463–5467 [1977]). A plasmid which encoded the correct ANP sequence, pB1325, was isolated and further subjected to site-directed mutagenesis (Kunkel) using an oligonucleotide with the sequence; 5'-AACAGCTTCCGTTACTAGGGCGGGCCC (SEQ ID NO: 44) to introduce an amber stop codon immediately following the codon for Tyr28 of the ANF sequence. The resulting plasmid, pB1537, contains the wild-type human ANF gene under the expression control of the alkaline phosphatase promoter, the trytophan Shine-Dalgarno sequence and the stII signal sequence. Shake flask experiments showed that pB1537 in 23G3 would secrete small amounts of ANF into the culture broth. However, some ANF variants in the same expression vector were found to express much higher amounts of protein.

EXAMPLE 24

Expression and Purification of Recombinant ANF Variant

ANF(1-28) R3D, G9T, R11S, M12L, R14S, G16R

Cultures of 34B8 pB1761T (see Example 23 for DNA consh-uction) were grown at 37° C. for about 24 hours in an aerated 10 liter fermentor in a low phosphate minimal media (Carter, P. et al., Biotechnology 10 pp 163–167, 1992) and containing 2 mg/ml carbenicillin. Glucose was added to maintain glucose excess or avoid anaerobiosis, depending on cell density, and the pH was maintained at pH 7.4 with the addition of $NH_4OH$. Cell density at harvest was about 100 $OD_{550}$.

Recombinant ANF containing the mutations R3D/G9T/R11S/M12L/R14S/G16R was purified as follows. The above cells were removed from 1 liter of fermentation culture by centrifugation at 6000 rpm (in Sorvall GS3 rotor) for 15 min, and the broth further clarified by filtration through a 0.45 micron membrane. The broth was brought to 0.1% TCA, incubated at room temperature for 30 minutes and centrifuged at 9000 rpm (in Sorvall GS3 rotor) for 30 minutes to remove any precipitable material. To the supernatant 1/10 volume of Nugel P-RP (Separation Industries) was added and gently mixed for 1 hour at room temperature. The reverse phase resin was then separated with a sintered glass filter and rinsed extensively with 0.1% TFA. The bound material was then eluted with 50% acetonitrile+0.1% TFA. The elute was then concentrated with a rotovap to remove the acetonitrile, and resuspended in 50 ml of 10 mM acetate buffer, pH 4.6. This solution was loaded onto a Mono S column, thoroughly rinsed with 20 mM acetate buffer, pH 4.6, and eluted with a 0–200 mM NaCl gradient in 20 mM acetate buffer, pH 4.6. The eluted fractions assayed to contain ANP activity were then pooled, concentrated by lyophilization, and resuspended in 5 ml of $dH_2O$. This sample was acidified (final 0.1% TFA), loaded onto a preparative Vydac C18 column and fractioned over a 0–30% acetonitrile+0.1% TFA gradient. A large dominant peak that occurred at about 16% acetonitrile was collected. Mass specroscopy, amino acid analysis and NMR showed this to the expected mutant ANP at a purity of greater than 95%. This material was lyophilized for storage.

EXAMPLE 25

ANF Variants

The ANF expression vector, pB1537, contains a f1 origin of replication that enables the production of single stranded DNA which can be used for site-directed mutagenesis of this plasmid. Oligonucleotides with the sequences 5'-GCCTATGCATCTCTGGATAGATCTAGCTGC (SEQ ID NO: 45) and 5'-AGATCTAGCTGCTTCACCGGCAGCCTGGATAGTATCAGAGCTCAGAGCGG (SEQ ID NO: 46) were used to separately introduce the ANF mutations R3D and G9T/R11S/M12L/R14S/G16R into pB1537 by site-directed mutagenesis as described by Kunkel (Kunkel, T. A. *Proc. Natl. Acad. Sci U.S.A.* 82:488–492 [1985]). To produce a mutant combining the mutations generated from both oligonucleotides the ~900 bp Bgl II-Styl DNA fragment from the R3D mutant was ligated to the ~4000 bp Bgl II-Styl DNA fragment of the G9T/R11S/M12L/R14S/G16R mutant. The resulting plasmid codes for the ANF mutant R3D/G9T/R11S/M12L/R14S/G16R is referred to as pB1761T.

All references described herein are expressly incorporated by reference.

What is claimed is:

1. A compound represented by Formula (I)

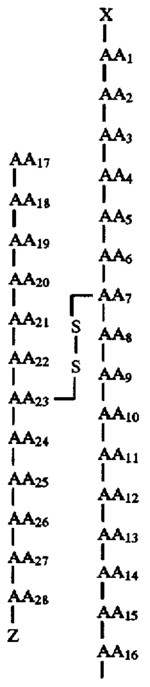

(I)

where

X is selected from the group consisting of H, $C_1$–$C_6$alkanoyl, Ser-Pro-Lys-, Thr-Ala-Pro-Arg-(SEQ ID NO: 1) and $C_1$–$C_6$alkanoyl-Thr-Ala-Pro-Arg-(SEQ ID NO: 1);

$AA_1$ is absent or is selected from the group consisting of Ser, Met, Gly, Asp, Ala, Tyr and His;

$AA_2$ is absent or is selected from the group consisting of Leu, Asp, Met, Val, Ser, Ala, Phe, Pro and Lys;

$AA_3$ is absent or is selected from the group consisting of Cys, Glu, Ser, Gln, His, Gly, Arg and Asp;

$AA_4$ is absent or is selected from the group consisting of Arg, Gly, Ala, Asp, Met, Leu, Tyr and Pro;

$AA_5$ is absent or is selected from the group consisting of Ser, Cys and Asp;

$AA_6$ is absent or is selected from the group consisting of Ser, Gly and Glu;

$AA_7$ is selected from the group consisting of Cys, N-methyl-Cys, D-Cys and Pen;

$AA_8$ is selected from the group consisting of Phe, N-methyl-Phe, Trimethylphenyl-Ala, halo(F, Cl, Br and I)phenyl-Ala, Trifluoromethylphenyl-Ala, Tyr, O-methyl-Tyr, Cha, β-napthyl-Ala, α-napthyl-Ala, biphenyl-Ala, diphenyl-Ala, D-Ala, dibenzyl-Ala, florenyl-Ala, adamantyl-Ala, and α-napthyloxy-Ala;

$AA_9$ is selected from the group consisting of Gly, Arg, Thr, Val, Asp, Ala, D-Ala, Pro and Glu;

$AA_{10}$ is selected from the group consisting of Gly, Arg, Ser, Ala, His, Pro and Lys;

$AA_{11}$ is selected from the group consisting of Arg, Lys, N-methyl-Arg, Asp, Ser and Pro;

$AA_{12}$ is selected from the group consisting of Met, Ile, D-Leu, Nle and Leu;

$AA_{13}$ is selected from the group consisting of Asp and Glu;

$AA_{14}$ is selected from the group consisting of Arg, N-methyl-Arg, Pro and Ser;

$AA_{15}$ is selected from the group consisting of Ile, N-Methyl-Ile and Leu;

$AA_{16}$ is selected from the group consisting of Gly, Tyr, Phe, Ser, Pro and a positively charged amino acid residue selected from Orn, Har, Lys, ρ-amidinophenyl-Ala and Arg;

$AA_{17}$ is selected from the group consisting of Ala, Ser, N-methyl-Ala, and Pro;

$AA_{18}$ is selected from the group consisting of Gln, Ser and homo-Cys;

$AA_{19}$ is Ser;

$AA_{20}$ is selected from the group consisting of Gly and Ala;

$AA_{21}$ is Leu;

$AA_{22}$ is selected from the group consisting of Gly and Ala;

$AA_{23}$ is Cys;

$AA_{24}$ is Asn;

$AA_{25}$ is selected from the group consisting of Ser and Val;

$AA_{26}$ is selected from the group consisting of Phe, D-Phe, N-methyl-Phe and Leu;

$AA_{27}$ is selected from the group consisting of Arg, Orn, Har, Lys, ρ-amidinophenyl-Ala and Arg-Arg;

$AA_{28}$ is selected from the group consisting of Tyr, Arg, Orn, Har, Lys, ρ-amidinophenyl-Ala, and homoCys; and Z is selected from the group consisting of OH and $NR^1R^2$ where $R^1$ and $R^2$ are independently selected from the group consisting of H, $C_1$–$C_4$alkyl, $C_6$–$C_{12}$aryl and $C_6$–$C_{12}$aryl-$C_1$–$C_6$alkyl; and where the amide bond (—C(=O)—NH—) bonding residues $AA_7$ and $AA_8$ may optionally be replaced with an amide isostere selected from the group consisting of $—CH_2—NH—$, $—CH_2—S—$, $—CH_2—S(O)_n—$, where n is 1 or 2, $—CH_2—CH_2—$, —CH=CH— (E or Z), $—C(=O)—CH_2—$,

—CH(CN)—NH—, $—C(OH)—CH_2—$, and

—O—C(=O)—NH— provided that at least two of $AA_9$, $AA_{11}$, and $AA_{16}$ are selected according to the following scheme $AA_9$ is Arg, Thr or Glu;

$AA_{11}$ is Asp, Ser or Pro; and $AA_{16}$ is a positively charged amino acid residue selected from the group consisting of Arg, homoArg, Lys, Orn, and ρ-amidinophenyl-Ala; and pharmaceutically acceptable salts thereof.

2. A compound represented by Formula (II) (SEQ ID NO: 47)

(II)

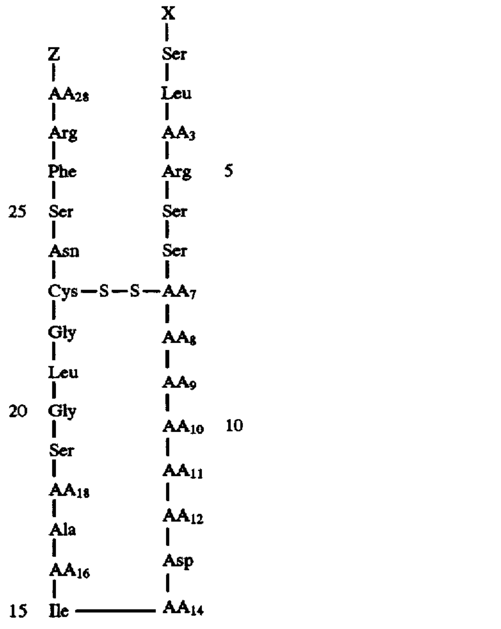

where

X is selected from the group consisting of H, $C_1$–$C_6$alkanoyl, and Thr-Ala-Pro-Arg-(SEQ ID NO: 1);

$AA_3$ is selected from the group consisting of Arg or Asp;

$AA_7$ is selected from the group consisting of Cys, N-methyl-Cys, D-Cys and Pen;

$AA_8$ is selected from the group consisting of Phe, N-methyl-Phe, trimethylphenyl-Ala, fluorophenyl-Ala, trifluoromethylphenyl-Ala, Tyr, O-methyl-Tyr, Cha, β-napthyl-Ala, α-napthyt-Ala, biphenyl-Ala, diphenyl-Ala, dibenzyl-Ala, florenyl-Ala, adamantyl-Ala, 2-thienyl-Ala and β-napthyloxy-Ala;

$AA_9$ is selected from the group consisting of Gly, Arg, Thr, Val, Asp and Glu;

$AA_{10}$ is selected from the group consisting of Gly, Arg, Ser, Ala, His and Lys;

$AA_{11}$ is selected from the group consisting of Arg, Asp, Ser and Pro;

$AA_{12}$ is selected from the group consisting of Met, Ile, D-Leu, Leu and Nle;

$AA_{14}$ is selected from the group consisting of Arg and Ser;

$AA_{16}$ is selected from the group consisting of Gly, Phe, Tyr, and a positively charged amino acid residue selected from Orn, Har, Lys, ρ-amidinophenyl-Ala and Arg;

$AA_{18}$ is selected from the group consisting of Gln and homoCys;

$AA_{28}$ is selected from the group consisting of Tyr and homoCys; and

Z is selected from the group consisting of OH and $NH_2$; and where the amide bond (—C(=O)—NH—) bonding residues $AA_7$ and $AA_9$ may optionally be replaced with an amide isostere selected from the group consisting of $—CH_2NH—$, $—CH_2—S—$, $—CH_2—S(O)_n—$, where n is 1 or 2, $—CH_2—CH_2—$, —CH=CH— (E or Z),

—C(=O)—CH—,

—CH(CN)—NH—, $—C(OH)—CH_2—$, and

—O—C(=O)—NH— provided that at least two of $AA_9$, $AA_{11}$, and $AA_{16}$ are selected according to the following scheme $AA_9$ is Arg, Thr or Glu;

$AA_{11}$ is Asp, Ser or Pro; and $AA_{16}$ is a positively charged amino acid residue selected from the group consisting of Orn, homoArg, Lys, ρ-amidinophenyl-Ala and Arg; and pharmaceutically acceptable salts thereof.

3. The compound of claim 2 further comprising inserting a D-amino acid residue between $AA_7$ and $AA_8$.

4. The compound of claim 2 wherein $AA_{16}$ is a positively charged amino acid residue selected from the group consisting of Orn, homoArg, Lys, ρ-amidinophenyl-Ala and Arg.

5. The compound of claim 4 wherein $AA_{16}$ is Arg.

6. The compound of claim 5 wherein X is Thr-Ala-Pro-Arg-(SEQ ID NO: 1).

7. The compound of claim 2 wherein $AA_9$ is Arg, Thr or Glu.

8. The compound of claim 7 wherein $AA_{11}$ is Asp, Ser or Pro.

9. The compound of claim 2 wherein $AA_{11}$ is Asp, Ser or Pro.

10. The compound of claim 2 having an increased half-life relative to wild-type hANF(1-28) when incubated with neutral endopeptidase 11.24.

11. A human ANF variant selected from the group consisting of hANF(1-28) G9T, R11S, M12I;

hANF(1-28) G9R, R11D, M12I, G16R;

hANF(1-28) G9T, R11S;

hANF(1-28) G9E, G10R, R11P;

hANF(1-28) G10K, R11S;

hANF(1-28) M12I, G16R;

hANF(1-28) G9T, R11S, G16R, Q18P;

hANF(TAPR 1-28) M12I, G16R;

hANF(1-28) M12I, R14S, G16R;

hANF(1-28) G9E, G10R, R11P, M12I, G16R;

hANF(1-28) R3D, G9T, R11S, M12L, R14S, G16R;

hANF(1-28) G9T, R11S, M12I, G16R, inserting D-Ser between residues 7 and 8;

hANF(1-28) G9T, R11S, M12I, G16R, inserting D-Ala between residues 7 and 8;

hANF(TAPR1-28) G9T, R11S, M12I, G16R;

hANF(1-28) F8Cha(1-cyclohexylalanine), G9T, R11S, M12I, G16R;

Mpa(mercaptopropionic acid), hANF(8-28) G9(D-Thr), R11S, M12I, G16R;

Mpa (mercaptopropionic acid), hANF(8-28) G9(D-Ala), R11S, M12I, G16R;

bANF(1-28) C7(N-MeCys), G9T, R11S, M12I, G16R;

hANF(1-28) F8(N-MePhe), G9T, R11S, M12I, G16R;

hANF(1-28) C7F8 replaced by C($\psi CH_2NH$)F, G9T, R11S, M12I, G16R;

hANF(1-28) G9(D-Ala), R11D, M12I, G16R;

hANF(1-28) F8Phg(D- or L-phenyl glycine), G9T, R11S, M12I, G16R;

hANF(1-28) R3D, G9T, R11S, M12L, R14S, G16R, Q18C, Y28C; and hANF(1-28) M12I, G16R, A17E, Q18A.

12. A pharmaceutical composition comprising a pharmaceutically acceptable excipient and the compound of claim 2.

13. A method for treating a disorder of electrolyte balance in a mammal comprising administering a therapeutically effective amount of the composition of claim 12 to the mammal.

14. A method for inducing natruresis, diuresis or vasodilation comprising administering to a mammal in need of such treatment a therapeutically effective amount of the composition of claim 12.

* * * * *

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( x i ) SEQUENCE DESCRIPTION: SEQ ID NO:1:

Thr Ala Pro Arg
1 4

( 2 ) INFORMATION FOR SEQ ID NO:2:

( i ) SEQUENCE CHARACTERISTICS:
( A ) LENGTH: 32 amino acids
( B ) TYPE: amino acid
( D ) TOPOLOGY: linear ( x i ) SEQUENCE DESCRIPTION: SEQ ID NO:2:

Thr Ala Pro Arg Ser Leu Arg Arg Ser Ser Cys Phe Gly Gly Arg
1 5 10 15

Met Asp Arg Ile Gly Ala Gln Ser Gly Leu Gly Cys Asn Ser Phe
20 25 30

Arg Tyr
32

( 2 ) INFORMATION FOR SEQ ID NO:3:

( i ) SEQUENCE CHARACTERISTICS:
( A ) LENGTH: 32 amino acids
( B ) TYPE: amino acid
( D ) TOPOLOGY: linear ( x i ) SEQUENCE DESCRIPTION: SEQ ID NO:3:

Ser Pro Lys Met Val Gln Gly Ser Gly Cys Phe Gly Arg Lys Met
1 5 10 15

Asp Arg Ile Ser Ser Ser Ser Gly Leu Gly Cys Asn Val Leu Arg
20 25 30

Arg Tyr
32

( 2 ) INFORMATION FOR SEQ ID NO:4:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:4:

Gly Leu Ser Lys Gly Cys Phe Gly Leu Lys Leu Asp Arg Ile Gly
1 5 10 15

Ser Met Ser Gly Leu Gly Cys
20 22

( 2 ) INFORMATION FOR SEQ ID NO:5:

( i ) SEQUENCE CHARACTERISTICS:
( A ) LENGTH: 32 amino acids
( B ) TYPE: amino acid -continued ( D ) TOPOLOGY: linear ( x i ) SEQUENCE DESCRIPTION: SEQ ID NO:5:

Thr Ala Pro Arg Ser Leu Arg Arg Ser Ser Cys Phe Gly Gly Arg
1 5 10 15

Ile Asp Arg Ile Arg Ala Gln Ser Gly Leu Gly Cys Asn Ser Phe
20 25 30

Arg Tyr
32

( 2 ) INFORMATION FOR SEQ ID NO:6:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:6:

Ser Leu Arg Arg Ser Ser Cys Phe Gly Gly Arg Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:7:

( i ) SEQUENCE CHARACTERISTICS:
( A ) LENGTH: 15 amino acids
( B ) TYPE: amino acid
( D ) TOPOLOGY: linear ( x i ) SEQUENCE DESCRIPTION: SEQ ID NO:7:

Ser Ser Cys Xaa Phe Gly Gly Arg Ile Asp Arg Ile Cys Phe Arg
1 5 10 15

( 2 ) INFORMATION FOR SEQ ID NO:8:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:8:

Ser Leu Arg Arg Ser Ser Cys Phe Thr Gly Ser Met Asp Arg Ile
1 5 10 15

Gly Ala Gln Ser Gly Leu Gly Cys Asn Ser Phe Arg Tyr
20 25 28

( 2 ) INFORMATION FOR SEQ ID NO:9:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:9:

Ser Leu Arg Arg Ser Ser Cys Phe Gly Gly Arg Ile Asp Arg Ile
1 5 10 15

Gly Ala Gln Ser Gly Leu Gly Cys Asn Ser Phe Arg Tyr
20 25 28

( 2 ) INFORMATION FOR SEQ ID NO:10:

( i ) SEQUENCE CHARACTERISTICS:
( A ) LENGTH: 28 amino acids
( B ) TYPE: amino acid ( D ) TOPOLOGY: linear ( x i ) SEQUENCE DESCRIPTION: SEQ ID NO:10:

Ser Leu Arg Arg Ser Ser Cys Phe Gly Gly Arg Ile Asp Ser Ile
1 5 10 15

Arg Ala Gln Ser Gly Leu Gly Cys Asn Ser Phe Arg Tyr
20 25 28

( 2 ) INFORMATION FOR SEQ ID NO:11:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:11:

Ser Leu Arg Arg Ser Ser Cys Phe Thr Gly Ser Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:12:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:12:

Ser Leu Arg Arg Ser Ser Cys Phe Arg Gly Asp Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:13:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:13:

Ser Leu Arg Arg Ser Ser Cys Phe Thr Gly Ser Ile Asp Arg Ile
1 5 10 15

Arg Ala Pro Ser Gly Leu Gly Cys Asn Ser Phe Arg Tyr
20 25 28

( 2 ) INFORMATION FOR SEQ ID NO:14:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:14:

Ser Leu Arg Arg Ser Ser Cys Phe Gly Lys Ser Met Asp Arg Ile
1 5 10 15

Gly Ala Gln Ser Gly Leu Gly Cys Asn Ser Phe Arg Tyr
20 25 28

( 2 ) INFORMATION FOR SEQ ID NO:15:

( i ) SEQUENCE CHARACTERISTICS:
( A ) LENGTH: 32 amino acids
( B ) TYPE: amino acid -continued ( D ) TOPOLOGY: linear ( x i ) SEQUENCE DESCRIPTION: SEQ ID NO:15:

Thr Ala Pro Arg Ser Leu Arg Arg Ser Ser Cys Phe Thr Gly Ser
1 5 10 15

Ile Asp Arg Ile Arg Ala Gln Ser Gly Leu Gly Cys Asn Ser Phe
20 25 30

Arg Tyr
32

( 2 ) INFORMATION FOR SEQ ID NO:16:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:16:

Ser Leu Arg Arg Ser Ser Cys Xaa Thr Gly Ser Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:17:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:17:

Ser Leu Arg Arg Ser Ser Xaa Phe Thr Gly Ser Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:18:

( i ) SEQUENCE CHARACTERISTICS:
( A ) LENGTH: 29 amino acids
( B ) TYPE: amino acid
( D ) TOPOLOGY: linear ( x i ) SEQUENCE DESCRIPTION: SEQ ID NO:18:

Ser Leu Arg Arg Ser Ser Cys Asn Xaa Thr Gly Ser Ile Asp Arg
1 5 10 15

Ile Arg Ala Gln Ser Gly Leu Gly Cys Asn Ser Phe Arg Tyr
20 25 29

( 2 ) INFORMATION FOR SEQ ID NO:19:

( i ) SEQUENCE CHARACTERISTICS:
( A ) LENGTH: 27 amino acids
( B ) TYPE: amino acid
( D ) TOPOLOGY: linear ( x i ) SEQUENCE DESCRIPTION: SEQ ID NO:19:

Ser Leu Arg Arg Ser Ser Xaa Thr Gly Ser Ile Asp Arg Ile Arg
1 5 10 15

Ala Gln Ser Gly Leu Gly Cys Asn Ser Phe Arg Tyr
20 25 27

( 2 ) INFORMATION FOR SEQ ID NO:20:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:20:

Xaa Phe Xaa Gly Asp Ile Asp Arg Ile Arg Ala Gln Ser Gly Leu
1 5 10 15

Gly Cys Asn Ser Phe Arg Tyr
20 22

( 2 ) INFORMATION FOR SEQ ID NO:21:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:21:

Ser Leu Arg Arg Ser Ser Cys Phe Gly Gly Arg Met Asp Arg Ile
1 5 10 15

Gly Ala Gln Ser Gly Leu Gly Cys Asn Ser Phe Arg Tyr
20 25 28

( 2 ) INFORMATION FOR SEQ ID NO:22:

( i ) SEQUENCE CHARACTERISTICS:
( A ) LENGTH: 32 amino acids
( B ) TYPE: amino acid
( D ) TOPOLOGY: linear ( x i ) SEQUENCE DESCRIPTION: SEQ ID NO:22:

Ser Pro Lys Met Val Gln Gly Ser Gly Cys Phe Gly Arg Lys Met
1 5 10 15

Asp Arg Ile Ser Ser Ser Ser Gly Leu Gly Cys Lys Val Leu Arg
20 25 30

Arg His
32

( 2 ) INFORMATION FOR SEQ ID NO:23:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:23:

Ser Leu Arg Arg Ser Ser Cys Phe Thr Gly Ser Met Asp Arg Ile
1 5 10 15

Arg Ala Gln Ser Gly Leu Gly Cys Asn Ser Phe Arg Tyr
20 25 28

( 2 ) INFORMATION FOR SEQ ID NO:24:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:24:

Ser Leu Arg Arg Ser Ser Cys Phe Thr Gly Ser Met Asp Arg Ile
1 5 10 15

Arg Ala Pro Ser Gly Leu Gly Cys Asn Ser Phe Arg Tyr
20 25 28

( 2 ) INFORMATION FOR SEQ ID NO:25:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:25:

```
Ser Leu Arg Arg Ser Ser Cys Phe Glu Arg Pro Met Asp Arg Ile
1               5                   10                  15

Gly Ala Gln Ser Gly Leu Gly Cys Asn Ser Phe Arg Tyr
                20                  25          28
```

( 2 ) INFORMATION FOR SEQ ID NO:26:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:26:

```
Ser Leu Asp Arg Ser Ser Cys Phe Thr Gly Ser Leu Asp Ser Ile
1               5                   10                  15

Arg Ala Gln Ser Gly Leu Gly Cys Asn Ser Phe Arg Tyr
                20                  25          28
```

( 2 ) INFORMATION FOR SEQ ID NO:27:

( i ) SEQUENCE CHARACTERISTICS:
( A ) LENGTH: 29 amino acids
( B ) TYPE: amino acid
( D ) TOPOLOGY: linear ( x i ) SEQUENCE DESCRIPTION: SEQ ID NO:27:

```
Ser Leu Arg Arg Ser Ser Cys Xaa Phe Thr Gly Ser Ile Asp Arg
1               5                   10                  15

Ile Arg Ala Gln Ser Gly Leu Gly Cys Asn Ser Phe Arg Tyr
                20                  25              29
```

( 2 ) INFORMATION FOR SEQ ID NO:28:

( i ) SEQUENCE CHARACTERISTICS:
( A ) LENGTH: 29 amino acids
( B ) TYPE: amino acid
( D ) TOPOLOGY: linear ( x i ) SEQUENCE DESCRIPTION: SEQ ID NO:28:

```
Ser Leu Arg Arg Ser Ser Cys Xaa Phe Thr Gly Ser Ile Asp Arg
1               5                   10                  15

Ile Arg Ala Gln Ser Gly Leu Gly Cys Asn Ser Phe Arg Tyr
                20                  25              29
```

( 2 ) INFORMATION FOR SEQ ID NO:29:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:29:

```
Xaa Phe Xaa Gly Ser Ile Asp Arg Ile Arg Ala Gln Ser Gly Leu
1               5                   10                  15

Gly Cys Asn Ser Phe Arg Tyr
                20      22
```

-continued ( 2 ) INFORMATION FOR SEQ ID NO:30:

( i ) SEQUENCE CHARACTERISTICS:
( A ) LENGTH: 22 amino acids
( B ) TYPE: amino acid
( D ) TOPOLOGY: linear ( x i ) SEQUENCE DESCRIPTION: SEQ ID NO:30:

```
Xaa Phe Xaa Gly Ser Ile Asp Arg Ile Arg Ala Gln Ser Gly Leu
  1               5                  10                  15

Gly Cys Asn Ser Phe Arg Tyr
                 20      22
```

( 2 ) INFORMATION FOR SEQ ID NO:31:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:31:

```
Ser Leu Arg Arg Ser Ser Xaa Phe Thr Gly Ser Ile Asp Arg Ile
  1               5                  10                  15

Arg Ala Gln Ser Gly Leu Gly Cys Asn Ser Phe Arg Tyr
                 20                  25          28
```

( 2 ) INFORMATION FOR SEQ ID NO:32:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:32:

```
Ser Leu Arg Arg Ser Ser Cys Xaa Thr Gly Ser Ile Asp Arg Ile
  1               5                  10                  15

Arg Ala Gln Ser Gly Leu Gly Cys Asn Ser Phe Arg Tyr
                 20                  25          28
```

( 2 ) INFORMATION FOR SEQ ID NO:33:

( i ) SEQUENCE CHARACTERISTICS:
( A ) LENGTH: 27 amino acids
( B ) TYPE: amino acid
( D ) TOPOLOGY: linear ( x i ) SEQUENCE DESCRIPTION: SEQ ID NO:33:

```
Ser Leu Arg Arg Ser Ser Xaa Thr Gly Ser Ile Asp Arg Ile Arg
  1               5                  10                  15

Ala Gln Ser Gly Leu Gly Cys Asn Ser Phe Arg Tyr
                 20                  25      27
```

( 2 ) INFORMATION FOR SEQ ID NO:34:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:34:

```
Ser Leu Arg Arg Ser Ser Cys Phe Xaa Gly Asp Ile Asp Arg Ile
  1               5                  10                  15

Arg Ala Gln Ser Gly Leu Gly Cys Asn Ser Phe Arg Tyr
                 20                  25          28
```

-continued ( 2 ) INFORMATION FOR SEQ ID NO:35:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:35:

Ser Leu Arg Arg Ser Ser Cys Xaa Thr Gly Ser Ile Asp Arg Ile
1 5 10 15

Arg Ala Gln Ser Gly Leu Gly Cys Asn Ser Phe Arg Tyr
20 25 28

( 2 ) INFORMATION FOR SEQ ID NO:36:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:36:

Ser Leu Asp Arg Ser Ser Cys Phe Thr Gly Ser Leu Asp Ser Ile
1 5 10 15

Arg Ala Cys Ser Gly Leu Gly Cys Asn Ser Phe Arg Cys
20 25 28

( 2 ) INFORMATION FOR SEQ ID NO:37:

( i ) SEQUENCE CHARACTERISTICS:
( A ) LENGTH: 28 amino acids
( B ) TYPE: amino acid
( D ) TOPOLOGY: linear ( x i ) SEQUENCE DESCRIPTION: SEQ ID NO:37:

Ser Leu Asp Arg Ser Ser Cys Phe Thr Gly Ser Leu Asp Ser Ile
1 5 10 15

Arg Ala Xaa Ser Gly Leu Gly Cys Asn Ser Phe Arg Xaa
20 25 28

( 2 ) INFORMATION FOR SEQ ID NO:38:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:38:

TCTCTGCGTA GATCTAGCTG CTTCGGCGGC CGCATG 36

( 2 ) INFORMATION FOR SEQ ID NO:39:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( x i ) SEQUENCE DESCRIPTION: SEQ ID NO:39:

GATCGTATCG GAGCTCAGAG CGGTCTCGGG TGCAA 35

( 2 ) INFORMATION FOR SEQ ID NO:40:

( i ) SEQUENCE CHARACTERISTICS:
( A ) LENGTH: 24 bases
( B ) TYPE: nucleic acid

-continued ( C ) STRANDEDNESS: single
( D ) TOPOLOGY: linear ( x i ) SEQUENCE DESCRIPTION: SEQ ID NO:40:

CAGCTTCCGT TACGTAGGCG GGCC 24

( 2 ) INFORMATION FOR SEQ ID NO:41:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( x i ) SEQUENCE DESCRIPTION: SEQ ID NO:41:

CAGCTAGATC TACGCAGAGA TGCA 24

( 2 ) INFORMATION FOR SEQ ID NO:42:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( x i ) SEQUENCE DESCRIPTION: SEQ ID NO:42:

TCTGAGCTCC GATACGATCC ATGCGGCCGC CGAAG 35

( 2 ) INFORMATION FOR SEQ ID NO:43:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( x i ) SEQUENCE DESCRIPTION: SEQ ID NO:43:

CGCCTACGTA ACGGAAGCTG TTGCACCCGA GACCGC 36

( 2 ) INFORMATION FOR SEQ ID NO:44:

( i ) SEQUENCE CHARACTERISTICS:
( A ) LENGTH: 27 bases
( B ) TYPE: nucleic acid
( C ) STRANDEDNESS: single
( D ) TOPOLOGY: linear ( x i ) SEQUENCE DESCRIPTION: SEQ ID NO:44:

AACAGCTTCC GTTACTAGGG CGGGCCC 27

( 2 ) INFORMATION FOR SEQ ID NO:45:

( i ) SEQUENCE CHARACTERISTICS:
( A ) LENGTH: 30 bases
( B ) TYPE: nucleic acid
( C ) STRANDEDNESS: single
( D ) TOPOLOGY: linear ( x i ) SEQUENCE DESCRIPTION: SEQ ID NO:45:

GCCTATGCAT CTCTGGATAG ATCTAGCTGC 30

( 2 ) INFORMATION FOR SEQ ID NO:46:

( i ) SEQUENCE CHARACTERISTICS:
( A ) LENGTH: 50 bases
( B ) TYPE: nucleic acid
( C ) STRANDEDNESS: single
( D ) TOPOLOGY: linear -continued ( x i ) SEQUENCE DESCRIPTION: SEQ ID NO:46:

AGATCTAGCT GCTTCACCGG CAGCCTGGAT AGTATCAGAG CTCAGAGCGG 50

( 2 ) INFORMATION FOR SEQ ID NO:47:

( i ) SEQUENCE CHARACTERISTICS:
( A ) LENGTH: 30 amino acids
( B ) TYPE: amino acid
( D ) TOPOLOGY: linear ( x i ) SEQUENCE DESCRIPTION: SEQ ID NO:47:

| | | | | | | | | | | | | | | |
|---|---|---|---|---|---|---|---|---|---|---|---|---|---|---|
| Xaa | Ser | Leu | Xaa | Arg | Ser | Ser | Xaa | Xaa | Xaa | Xaa | Xaa | Xaa | Asp | Xaa |
| 1 | | | | 5 | | | | | 10 | | | | | 15 |
| Ile | Xaa | Ala | Xaa | Ser | Gly | Leu | Gly | Cys | Asn | Ser | Phe | Arg | Xaa | Xaa |
| | | | | 20 | | | | | 25 | | | | | 30 |